US008541476B2

(12) United States Patent
Koumenis et al.

(10) Patent No.: US 8,541,476 B2
(45) Date of Patent: Sep. 24, 2013

(54) COMPOUNDS FOR TREATMENT OF MALIGNANT TUMORS

(75) Inventors: Constantinos Koumenis, Philadelphia, PA (US); Brian E. Lally, Miami, FL (US); Steven Kridel, Clemmons, NC (US); Gary D. Kao, Wynnewood, PA (US); Adeboye Adejare, Mantua, NJ (US)

(73) Assignees: The Trustees of the University of Pennsylvania, Philadelphia, PA (US); Wake Forest University Health Sciences, Winston-Salem, NC (US); University of the Sciences in Philadelphia, Philadelphia, PA (US)

( * ) Notice: Subject to any disclaimer, the term of this patent is extended or adjusted under 35 U.S.C. 154(b) by 279 days.

(21) Appl. No.: 12/677,478

(22) PCT Filed: Sep. 12, 2008

(86) PCT No.: PCT/US2008/076208
§ 371 (c)(1), (2), (4) Date: Apr. 6, 2011

(87) PCT Pub. No.: WO2009/036297
PCT Pub. Date: Mar. 19, 2009

(65) Prior Publication Data
US 2011/0190400 A1 Aug. 4, 2011

Related U.S. Application Data

(60) Provisional application No. 61/004,386, filed on Nov. 27, 2007, provisional application No. 60/993,776, filed on Sep. 14, 2007.

(51) Int. Cl.
*A61K 31/10* (2006.01)
*C07C 315/00* (2006.01)
*C40B 30/06* (2006.01)

(52) U.S. Cl.
USPC .......................................................... 514/709

(58) Field of Classification Search
USPC ............................... 514/709; 568/30; 506/10
See application file for complete search history.

(56) References Cited

U.S. PATENT DOCUMENTS

| 3,772,444 | A |   | 11/1973 | Sarett et al. |
|---|---|---|---|---|
| 3,953,539 | A |   | 4/1976 | Kawase et al. |
| 5,877,185 | A | * | 3/1999 | Kun et al. ................. 514/309 |
| 2005/0207972 | A1 |   | 9/2005 | Friebe et al. |
| 2006/0094750 | A1 |   | 5/2006 | Kon-I et al. |
| 2006/0167324 | A1 |   | 7/2006 | Hidaka et al. |
| 2006/0293392 | A1 |   | 12/2006 | Powers et al. |
| 2007/0037778 | A1 |   | 2/2007 | Kreft et al. |

OTHER PUBLICATIONS ptcl.chem.ox.ac.uk/MSDS structure activity relationship; Jaworska, 1-8, 2004.*
Cecil Text book of Medicine, 20th Edition vol. 1 W. B. Saunders Company, 1997, pp. 1004-1010.*
Bakkenist et al., "DNA damage activates ATM through intermolecular autophosphorylation and dimer dissociation." 2003, Nature 421:499-506.
Bassing et al., "Increased ionizing radiation sensitivity and genomic instability in the absence of histone H2AX." 2002, Proc. Natl. Acad. Sci. U.S.A. 99:8173-8178-.
Bonner et al., "Low-dose radiation: thresholds, bystander effects, and adaptive responses." 2003, Proc. Natl. Acad. Sci. U.S.A. 100:4973-4975.
Geiger et al., "Zebrafish as a "biosensor"? Effects of ionizing radiation and amifostine on embryonic viability and development." 2006, Cancer Res. 66:8172-8181.
Koumenis, et al., "Regulation of protein synthesis by hypoxia via activation of the endoplasmic reticulum kinase PERK and phosphorylation of the translation initiation factor eIF2alpha." 2002, Mol. Cell Biol. 22:7405-16.
Li et al., "Regulation of CHK2 by DNA-dependent Protein Kinase" 2005, J. Biol. Chem. 280:12041-12050.
Li, et al., "Modification of the ionizing radiation response in living cells by an scFv against the DNA-dependent protein kinase." 2003, Nucleic Acids Res. 31:5848-57.
Lipinski et al., "Experimental and computational approaches to estimate solubility and permeability in drug discovery and development settings." 2001, Adv. Drug Deliv. Rev. 46:3-26.
Lukas et al., "Mammalian cell cycle checkpoints: signalling pathways and their organization in space and time." 2004, DNA Repair (Amst.) 3(8-9):997-1007.
Macphail et al., "Expression of phosphorylated histone H2AX in cultured cell lines following exposure to X-rays." 2003, Int. J. Radiat. Biol. 79:351-358.
Matsuoka et al., "Linkage of ATM to Cell Cycle Regulation by the Chk2 Protein Kinase" 1998, Science 282:1893-1990.
McAleer et al., "Novel use of zebrafish as a vertebrate model to screen radiation protectors and sensitizers." 2005, Int. J. Radiat. Oncol. Biol. Phys. 61:10-13.
Nazarov et al., "Dephosphorylation of histone gamma-H2AX during repair of DNA double-strand breaks in mammalian cells and its inhibition by calyculin A." 2003, Radiat. Res. 160:309-317.
Olive et al., "Phosphorylation of histone H2AX as a measure of radiosensitivity." 2004, Int. J. Radiat. Oncol. Biol. Phys. 58:331-335.
Pandita et al., "Ionizing radiation activates the ATM kinase throughout the cell cycle." 2000, Oncogene 19:1386-1391.
Rogakou et al., "DNA double-stranded breaks induce histone H2AX phosphorylation on serine 139." 1998, J. Biol. Chem. 273:5858-5868.
Siino et al., "End-joining of reconstituted histone H2AX-containing chromatin in vitro by soluble nuclear proteins from human cells." 2002, FEBS Lett. 527:105-108.
Smart, et al., "Thioredoxin reductase as a potential molecular target for anticancer agents that induce oxidative stress." 2004, Cancer Res. 64:6716-24.
Steel et al., "Exploitable mechanisms in combined radiotherapy-chemotherapy: The concept of additivity" 1979, Int. J. Radiat. Oncol. Biol. Phys. 5:85-91.
Stiff et al., "ATM and DNA-PK function redundantly to phosphorylate H2AX after exposure to ionizing radiation." 2004, Cancer Res. 64:2390-2396.

(Continued)

*Primary Examiner* — Shirley V Gembeh
(74) *Attorney, Agent, or Firm* — Riverside Law LLP

(57) ABSTRACT

The present invention comprises compounds, compositions and methods of use for sensitizing cancer cells, tumors, neoplasms, and malignancies to the effects of ionizing radiation used in the treatment of cancer. The invention further comprises a method of identifying novel radiosensitizing compounds.

12 Claims, 16 Drawing Sheets

(56) References Cited

OTHER PUBLICATIONS

Suzuki et al., "A Mild and Efficient Debromination of Vicinal Dibromoalkanes With Sodium Telluride Prepared From Tellurium and Rongalite" 1985, Chem. Lett. 225-228.

Suzuki et al., "A Novel Synthesis of Alkyl Aryl Sulfones via the Telluride Ion-Assisted Coupling of Arenesulfonyl Chlorides with Alkyl Halides" 1988, Chem. Lett. 727-728.

Zhao, et al., "Preclinical evaluation of a potent novel DNA-dependent protein kinase inhibitor NU7441." 2006, Cancer Res. 66:5354-62.

* cited by examiner

A

COMPOUNDS FOR TREATMENT OF MALIGNANT TUMORS

CROSS-REFERENCE TO RELATED APPLICATIONS

This is a National Stage application of PCT International Application No. PCT/US2008/076208, filed Sep. 12, 2008, which in turn claims the benefit pursuant to 35 U.S.C. §119(e) of U.S. Provisional Application No. 60/993,776 filed on Sep. 14, 2007 and U.S. Provisional Application No. 61/004,386, filed Nov. 27, 2007 which are hereby incorporated by reference in their entirety herein.

STATEMENT REGARDING FEDERALLY SPONSORED RESEARCH OR DEVELOPMENT

This invention was made with government support under grant number T32CA113267, awarded by the National Institutes of Health. The government has certain rights in the invention.

BACKGROUND OF THE INVENTION

The prognosis for patients with glioblastoma multiforme (GBM) has improved only slightly over the last few decades. Randomized trials have shown that radiotherapy improves outcomes (Walker et al., 1980, N. Eng. J. Med. 303:1323-9) and results in a median survival of 12 months (Curran, et al., 1993, J. Natl. Cancer Inst. 85:704-10; Scott, et al., 1998, Int. J. Radiat. Oncol. Biol. Phys. 40:51-5). A recent prospective clinical trial found that radiotherapy combined with temozolomide significantly improved survival, albeit by a modest 2.5 months (Stupp, et al., 2002, N. Eng. J. Med. 352:987-96). Attempts have been made at increasing the radiation dose either with additional external beam radiotherapy (Chan, et al., 2002, J. Clin. Oncol. 20:1635-42), brachytherapy (Tatter, et al., 2003, J. Neurosurg. 99:297-303), or stereotactic radiosurgery (Regine, et al., 2000, J. Radiat. Oncol. Biol. Phys. 48:421-6), but no significant improvement in survival has been demonstrated. Thus, an agent which preferentially enhances the cytotoxic effects of radiation on glioma cells, but has minimal effects on the survival of normal brain cells, has the potential to improve the therapeutic result for these patients (Steel et al., 1979, J. Radiat. Oncol. Biol. Phys. 5:85-91).

The major cellular pathways leading to sensing and repairing radiation-induced damage have been extensively studied, and the mechanisms involved have become attractive targets for agents that have the potential to increase therapeutic gain when combined with IR. This approach has identified some promising candidates (Li, et al., 2003, Nucleic Acids Res. 31:5848-57; Smart, et al., 2004, Cancer Res. 64:6716-24; Zhao, et al., 2006, Cancer Res. 66:5354-62) which are currently being investigated at the preclinical stage.

There exists in the art a need for novel radiosensitizing compounds. There also exists in the art a need for novel methods of treatment of cancers which exploit radiosensitizing compounds. Further, there exists a need in the art for a method of rapidly screening and identifying novel radiosensitizing compounds. The present invention fills these needs.

SUMMARY OF THE INVENTION

In one embodiment, the invention comprises a composition comprising a compound of formula (I):

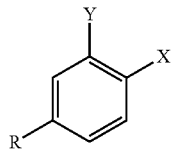

where
Y is $NO_2$, $NR^1_3$, CN, CHO, $C(O)R^1$ or $CF_3$;
X is H, F, Cl, Br or I;
R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable salt thereof, with the proviso that the composition excludes a compound of:
Formula I, where Y=$NO_2$, R=$C(O)R^1$, and $R^1$=$CH_2CH_3$, where X=F, Cl, Br, or H;
Formula I, where Y=$NO_2$, R=$S(O)_2R^1$, and $R^1$=$CH_2CH_3$, where X=Cl, Br, or H; and
Formula I, where Y=$NO_2$, R=$P(O)(OH)R^1$, $R^1$=$CH_2CH_3$, where X=H.

In one aspect, the invention comprises a pharmaceutically acceptable analogue, modification, derivative, adduct, pro-drug or solvate of the composition. In another aspect, the composition comprises a pharmaceutically acceptable carrier.

In another embodiment, the invention comprises a composition comprising Compound 1 of Formula I, where Y=$NO_2$, R=$C(O)R^1$, $R^1$=$CH_2CH_3$, and where X=I, or a pharmacologically acceptable salt thereof. In one aspect, the invention comprises a pharmaceutically acceptable analogue, modification, derivative, adduct, pro-drug or solvate of the composition.

In yet another embodiment, the invention comprises a composition comprising Formula I, where Y=$NO_2$, R=$S(O)_2R^1$, $R^1$=$CH_2CH_3$, designated Compound 2, where X=F or I, or a pharmaceutically acceptable salt thereof. In one aspect, the invention comprises a pharmaceutically acceptable analogue, modification, derivative, adduct, pro-drug or solvate of the composition.

In still another embodiment, the invention comprises a composition comprising Formula I, where Y=$NO_2$, R=$P(O)(OH)R^1$, $R^1$=$CH_2CH_3$, designated Compound 3, where X=F, Cl, Br, H, or I, or a pharmacologically acceptable salt thereof. In one aspect, the invention comprises a pharmaceutically acceptable analogue, modification, derivative, adduct, salt, pro-drug or solvate of the composition.

Another embodiment of the present invention comprises a method of identifying a radiosensitizer compound comprising a cell-based, high-throughput assay, the method comprising the steps of: a) culturing a cell in a multi-well plate; b) contacting the cell with a test compound; c) exposing the cell to 2-6 Gy radiation; d) assaying the cell 2-6 days later to assess cell survival, where, when the survival of the cell is reduced compared to a cell not contacted by the test compound, the test compound is identified as a radiosensitizer compound. In one aspect, the contacting of the cell with the test compound occurs before, during, or after exposing the cell to said radiation. In another aspect, the cell is a cancer cell. In still another aspect, the cell is an acutely isolated cancer cell. In yet another aspect, the cell is a cultured cancer cell. In another aspect, the cell is a cancer cell line. In still another aspect, the cell is selected from the group consisting of a U251 glioma cell, an HT-29 colorectal cell, and an A549 lung adenocarcinoma cell.

Another embodiment of the invention comprises a method of treating a mammal diagnosed with cancer, the method comprising administering to the mammal a therapeutically effective amount of a pharmacological composition comprising a compound of formula (I):

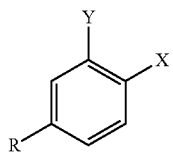

wherein
Y is $NO_2$, $NR^1_3$, CN, CHO, $C(O)R^1$ or $CF_3$;
X is H, F, Cl, Br or I;
R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable salt, where the composition contacts a cancer cell or tumor in the mammal, thereby making the cancer cell or tumor more susceptible to ionizing radiation. In one aspect, the composition is administered before, during, or after the mammal receives radiation therapy, or a combination thereafter. In another aspect, the mammal is a human.

Another embodiment of the invention comprises a method of treating a mammal diagnosed with cancer, the method comprising administering to the mammal a therapeutically effective amount of a composition comprising Formula I, where Y=$NO_2$, R=$C(O)R^1$, $R^1$=$CH_2CH_3$, and X=I, or a pharmaceutically acceptable salt thereof, where the composition contacts a cancer cell or tumor in the mammal, thereby making the cancer cell or tumor more susceptible to ionizing radiation. In one aspect, the composition is administered before, during, or after the mammal receives radiation therapy, or a combination thereafter. In another aspect, the mammal is a human.

Yet another embodiment of the invention comprises a method of treating a mammal diagnosed with cancer, the method comprising administering to the mammal a therapeutically effective amount of a composition comprising Formula I, where Y=$NO_2$, R=$S(O)_2R^1$, $R^1$=$CH_2CH_3$, and X=F or I, or a pharmaceutically acceptable salt thereof, wherein the composition contacts a cancer cell or tumor in the mammal, thereby making the cancer cell or tumor more susceptible to ionizing radiation. In one aspect, the composition is administered before, during, or after the mammal receives radiation therapy, or a combination thereafter. In another aspect, the mammal is a human.

Still another embodiment of the invention comprises a method of treating a mammal diagnosed with cancer, said method comprising administering to said mammal a therapeutically effective amount of a composition comprising Formula I, Y=$NO_2$, R=$P(O)(OH)R^1$, $R^1$=$CH_2CH_3$, and X=F, Cl, Br, H, or I, or a pharmaceutically acceptable salt thereof, wherein said composition contacts a cancer cell or tumor in said mammal, thereby making said cancer cell or tumor more susceptible to ionizing radiation. In one aspect, the composition is administered before, during, or after the mammal receives radiation therapy, or a combination thereafter. In another aspect, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A and FIG. 1B, is a series of images illustrating the structures of various radiosensitizing compounds identified and used in the methods of the instant invention. FIG. 1A (1) depicts the structure of 4'-bromo-3'-nitropropiophenone (NS-123). FIG. 1A (2) depicts the structure of 4-bromo-3-nitrobenzonitrile (NS-160). FIG. 1B depicts the structures of three radiosensitizing compounds. FIG. 1B (1) is a schematic diagram of Formula I, where Y=$NO_2$, R=$C(O)R^1$, and $R^1$=$CH_2CH_3$, designated Compound 1. FIG. 1B (2) is a schematic diagram of Formula I, where Y=$NO_2$, R=$S(O)_2R^1$, and $R^1$=$CH_2CH_3$, designated Compound 2. FIG. 1B (3) is a schematic diagram of Formula I, where Y=$NO_2$, R=$P(O)(OH)R^1$, $R^1$=$CH_2CH_3$, designated Compound 3. For each of these compounds, X can be F, Cl, Br, H, or I as indicated at the bottom of FIG. 1B and described in the specification.

FIG. 3B depicts dose-dependent effects of NS-123 on U251 cell survival. U251 cells were treated with the indicated doses of NS-123. FIG. 1D depicts time-dependent effects of NS-123 on U251 cell survival. U251 cells were treated with 5.0 μM of NS-123 for the indicated time with NS-123. Results represent the averages of N=3 experiments±S.E.M.

FIG. 4A through FIG. 4D, is a series of graphs depicting the radiosensitizing effect of NS-123 on U251 glioma, HT-29 colorectal carcinoma, and A549 lung adenocarcinoma cells in a dose- and time-dependent manner. FIG. 4A is a graph depicting U251 cells treated with NS-123 for 12 hours at the indicated doses. FIG. 4B is a graph depicting U251 cells treated with NS-123 at the times indicated before irradiation. Calculated Dose Enhancement Ratios (DER) at 0.1 survival are: (A): 1.3 for 2.5 μM and 2.0 for 5.0 μM; (B): 1.2, for 4 hours, 1.4 for 8 hours, and 1.9 for 12 hours pretreatment. FIG. 4C is a graph depicting HT-29 colorectal cancer cells treated with DMSO (control) or 5 μM NS-123 for 12 hours prior to IR. DER at 0.5 survival is 3.0. FIG. 4D is a graph depicting A549 lung tumor cells treated with DMSO (control) or 5 μM NS-123 for 12 hours prior to IR. DER at 0.1 survival is 1.4. Results represent the averages of N=3 experiments±S.E.M.

FIG. 5A through FIG. 5C, is a series of images depicting the effect of NS-123 on non-cancerous tissue. FIG. 5A is a graph depicting that NS-123 does not radiosensitize normal human glial cells. Modified MTS assays performed on normal human glial cells in the presence or absence of NS-123 following IR. Results are the average of 2 independent experiments, and each experiment was performed in quadruplicate (N=4 wells). FIG. 5B is a graph depicting that NS-123 does not potentiate adverse effects of IR on zebrafish (ZF) development. ZF embryos were pretreated for 8 hours with 5 μM NS-123 prior to 6 Gy of IR at 16 hours-post fertilization (hpf). Pretreatment for 8 hours with 1 μM Staurosporine (SRS), a known radiosensitizer of both normal and tumor cells was used a positive control. Each point in the graph in (A) is the average of 60-140 embryos. FIG. 5C is a series of photomicrographs depicting the morphologic effects of ionizing radiation in the developing ZF. The effects of NS-123 on morphology were also evaluated for each group with representative photographs shown. NS-123+IR induced minimal changes. When ZF where irradiated in the presence of SRS, morphologic changes consistent with increased toxicity were demonstrated including shorten body length, spine curvature, and pericardial edema.

FIG. 6A through FIG. 6C, is a series of images depicting the effect of NS-123 on U251 cell xenografts sensitivity to IR in ZF embryos. FIG. 6A is a series of images depicting U251-RFP cells in culture at 30° C. for 7 days (left panel). Fluorescently labeled cells in a ZF embryo at 3 days post fertilization (dpf) (middle panel). Lateral merged phase and fluorescent image view of an embryo at 18 hpf, 2 hours after transplantation, showing approximately 150 human glioma cells transplanted into the yolk sac observed at the same magnification (right panel). Scale bar=75 μm in middle panel, 100 μm in right panel. FIG. 6B is a series of images depicting that irradiation in the presence of NS-123 further decreases the proportion of surviving human glioma cells in ZF embryos. Lateral views of live ZF embryos after transplantation of fluorescently labeled human glioma cells. Top row: 1 dpf, ZF embryos are photographed immediately prior to irradiation with 10 Gy; Middle row: At 3 dpf; Bottom row: At 5 dpf. FIG. 6C is a chart depicting histograms showing the relative levels of fluorescence from A-B displayed in arbitrary units of luminescence from triplicate experiments.

FIG. 7A and FIG. 7B, is a series of graphs depicting the ability of nu/nu mice to tolerate NS-123 and the ability of NS-123 to induce radiosensitization in tumor xenografts. FIG. 7A is a graph depicting the mass (gm) of three nu/nu mice injected with 50 mg/kg of NS-123 on 3 consecutive days, each day of injection indicated by ↓ on the X-axis. The plots of each animal weight were fit with a first order linear regression; all mice slightly increased in weight. FIG. 7B is a graph depicting the effect of NS-123 on tumor growth in vivo. Tumors were treated with 50 mg/kg of NS-123, or a similar volume of DMSO, for 3 consecutive days indicated by ↓ on the X-axis. Four hours after the second injection, the mice were treated with Sham IR or 5 Gy IR, indicated by the ‡ on the X-axis.

FIG. 8A and FIG. 8B, is a series of images depicting the effect of NS-123 on DNA repair. FIG. 8A is a graph depicting NS-123 inhibition of dsDNA break repair. Double strand break (DSB) processing was measured using pulse field gel electrophoresis (PFGE) and number average length analysis (KALA) after exposure to 4 Gy of γ-rays. Values are normalized to the initial maximum yields for each cell line and are averages from three independent irradiation experiments. Error bars, SEM; in some cases are smaller than the corresponding symbol. FIG. 8B is an image of an immunoblot depicting NS-123 prolongation of dsDNA damage-dependent signaling following IR. Cells were treated with DMSO (control) or 30 μM NS-123 for 4 h prior to IR. Immunoblotting was performed with an anti-γ-H2AX antibody, an anti-P-CHK2 antibody, anti-P-ATM, or anti-P-DNA-PKcs antibody, followed by incubation with secondary anti-mouse-IgG-HRP or anti-rabitt-IgG-HRP antibody. Immunoblotting for β-actin or DNA-PKcs was used as a loading control.

FIG. 10A and FIG. 10B, is a series of graphs depicting the results of clonogenic survival of HT-29 human colorectal tumor cells in the presence of two chemical analogs of NS-123. FIG. 10A is a graph depicting a comparison of clonogenic survival in the presence of Formula I, where Y=NO$_2$, R=C(O)R$^1$, and R$^1$=CH$_2$CH$_3$, and X=H (Compound 1D; 5 microM) or the vehicle control DMSO. FIG. 10B is a graph depicting a comparison of clonogenic survival in the presence of Formula I, where Y=NO$_2$, R=S(O)$_2$R$^1$, and R$^1$=CH$_2$CH$_3$, where X=Br (Compound 2C; 2.5 microM) or the vehicle control DMSO. In both cases, cells were pretreated with the compounds or DMSO vehicle control for 4 h prior to treatment with ionizing radiation at the indicated doses.

DETAILED DESCRIPTION OF THE INVENTION

Figure 1:
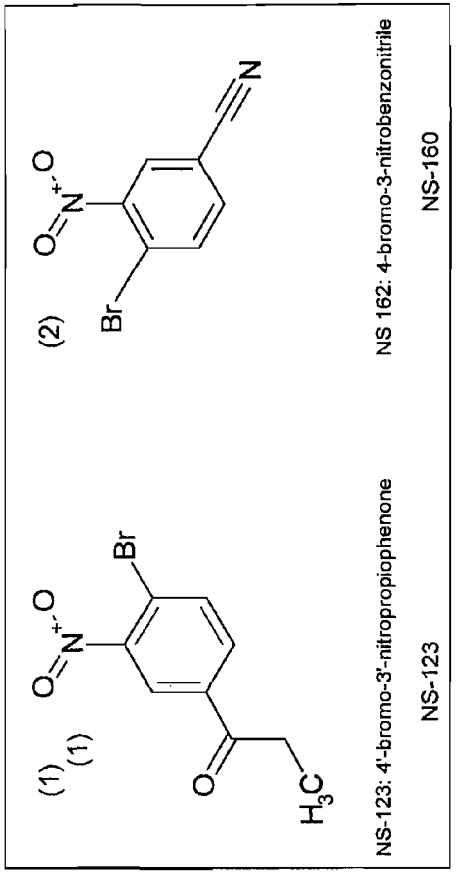
FIG. 1, comprising
Figure 1:
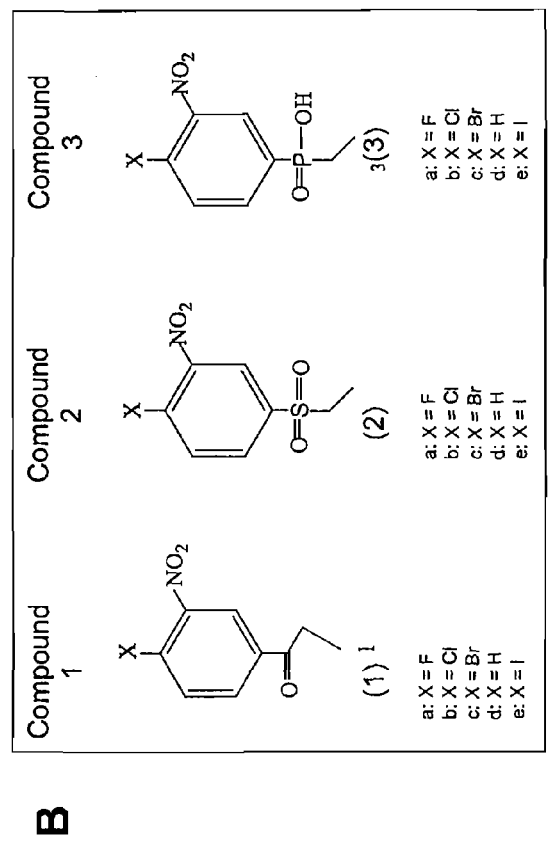

The present invention springs from the development and implementation of a novel, cell-based screening assay that allows the rapid and efficient identification of radiosensitizing molecules and compounds. As such, the present invention encompasses novel radiosensitizing compounds identified using the assay of the present invention, as well as a method of treating cancer using a radiosensitizing compound identified using the assay of the present invention.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, an intravenous infusion, topical cream and the like, for administering a radiosensitizer, such as a chemical compound, an antibody, a siRNA, a nucleic acid, protein, and/or composition of the invention to a mammal.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, chemical compound and/or composition of the invention or be shipped together with a container, which contains the nucleic acid, peptide, chemical composition, and/or composition. Alternatively, the instructional material may be shipped separately from the container with the intention that the instructional material and the compound be used cooperatively by the recipient.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

As used herein, to "treat" means reducing the frequency with which symptoms of a disease, are experienced by a patient, or altering the natural history and/or progression of a disease in a patient.

A "portion" of a polynucleotide means at least at least about fifteen to about fifty sequential nucleotide residues of the polynucleotide. It is understood that a portion of a polynucleotide may include every nucleotide residue of the polynucleotide.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when a radiosensitizer is administered compared with the onset and/or symptoms in the absence of the inhibitor.

A "radiosensitizer" or "radiosensitizing agent, molecule, or compound," as the term is used herein, means an agent, molecule, or compound that enhances the sensitivity of a neoplastic call, a cancer cell or a tumor to the effects of radiation. The "sensitivity" of a neoplastic cell, a cancer cell, or a tumor to radiation is the susceptibility of the neoplastic cell, cancer cell, or tumor to the inhibitory effects of radiation on the cell's or tumor's growth and/or viability.

The phrase "reduction of growth," as used herein, refers to any reduced growth, replication rate, or colony formation exhibited by a neoplastic cell, a cancer cell, or a tumor in response to some therapeutic agent, treatment, or clinical intervention, such as radiation. For example, a neoplastic cell may exhibit a reduction in the cell's growth rate or its ability to replicate and form colonies in vitro or in vivo (e.g, when implanted as a tumor in an animal) in response to radiation.

The phrase "reduction in viability," as used herein, refers to any reduction in survival exhibited by a neoplastic cell, a cancer cell, or a tumor in response to some therapeutic agent, treatment, or clinical intervention, such as radiation. A neoplastic cell, a cancer cell, or a tumor may exhibit reduced viability in response to radiation by inhibition of progression of the cell through the cell cycle; damaged nucleic acids, proteins, or other macromolecules in a cell, induced terminal differentiation (senescence), in which the cell no longer replicates; inhibited cellular repair of nucleic acids; or increased rates of cell death by inducing apoptosis or "mitotic catastrophe"—a form of necrosis, when DNA damage levels are beyond those that can be effectively repaired.

A neoplastic cell that is "resistant" to radiation is a neoplastic cell not killed or substantially growth inhibited by radiation. To determine if a neoplastic cell is substantially growth inhibited, the growth rate of the cell in the presence or absence of radiation can be determined by established methods in the art, such as cell counts, MTT assays and clonogenic survival assays, in which cell colonies (formed by replicating tumor cells) are formed and counted. The neoplastic cell is not growth inhibited by radiation if the growth rate is not significantly different with or without radiation, or if the cell cannot form a colony.

A tumor that is "resistant" to radiation is a tumor of which the rate of size increase or weight increase does not substantially change in the presence of radiation. Alternatively, if the subject bearing the tumor displays similar symptoms or indicators of the tumor whether the subject receives radiation or not, the tumor is resistant to radiation.

A "neoplastic cell," "cancer cell," "tumor cell," or "cell with a proliferative disorder," refers to a cell which proliferates at an abnormally high rate. A new growth comprising neoplastic cells is a neoplasm, also known as a "tumor". A tumor is an abnormal tissue growth, generally forming a distinct mass, that grows by cellular proliferation more rapidly than normal tissue growth. A tumor may show partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant tumors arising from epithelial structures are called carcinomas, malignant tumors that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other tumors include, but are not limited to neurofibromatosis.

A "lesion" is an injury, wound or an area that is structurally abnormal. In the context of a subject bearing tumor, a lesion is a tumor mass unless otherwise described.

A "therapeutic" treatment is a treatment administered to a subject who exhibits signs of pathology for the purpose of diminishing or eliminating those signs.

An "effective amount" is an amount of an irradiating agent or chemotherapeutic agent which is sufficient to result in the intended effect. For an irradiating agent used to treat or ameliorate a tumor, an effective amount is an amount of the irradiating agent sufficient to alleviate or eliminate the symptoms of the tumor, or to slow down the progress of the tumor. For a compound to sensitize a tumor to an irradiating agent, an effective amount is an amount of the compound sufficient to increase sensitivity of the tumor to the irradiating agent.

As used herein, the language "pharmaceutically acceptable salt" refers to a salt of the administered compounds prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

As used herein, the term "prodrug" refers to a pharmacological substance, drug, formulation or compound that is administered to a subject in an inactive form. Once administered, the prodrug is metablized in vivo into an active metabolite. A prodrug must undergo chemical conversion by metabolic processes before becoming an active pharmacological agent.

The term "solvate," as used herein, refers to a compound formed by solvation.

The term "solvation," as used herein refers to the process of attraction and association of molecules of a solvent with molecules or ions of a solute. As ions dissolve in a solvent they spread out and become surrounded by solvent molecules.

Description

The present invention encompasses the identification of radiosensitizing compounds that increase sensitivity of a cancer cell or a tumor to the effects of ionizing radiation used in the treatment of cancer. The compounds of the present invention do not have a similar effect on normal tissue, non-cancerous tissue, or on embryonic tissue. Further, the present invention discloses a cell-based assay for screening potential radiosensitizing compounds for use as radiosensitizers. The present invention also provides a method of treating a subject diagnosed with a cancer or tumor by administering to the subject a therapeutically effective amount of a radiosensitizing compound of the present invention.

I. Compositions

The invention includes a radiosensitizing compound that renders a cancer cell more susceptible to the effects of ionizing radiation used as a cancer therapy.

As used herein, the term "effects of radiation" or "effects of ionizing radiation" refers to the well known cytostatic and cytotoxic effects that radiation has on a cell. For example, exposure of a cell to radiation can inhibit progression of the cell through the cell cycle; can damage nucleic acids, proteins, or other macromolecules in a cell; can induce terminal differentiation (senescence), in which the tumor cell no longer replicates; can prevent cellular repair of nucleic acids; or can kill the cell by inducing apoptosis or "mitotic catastrophe"—a form of necrosis, when DNA damage levels are beyond those that can be effectively repaired. It should be recognized that these effects of radiation are interrelated and represent a continuum of effects, the magnitude of which is dependent, in part, on the radiation dose and on the relative radiosensitivity of the target cell.

In one embodiment of the invention, a radiosensitizing compound increases the sensitivity of a cancer cell or a tumor to the effects of ionizing radiation used in the treatment of cancer. In another embodiment of the invention, a radiosensitizing compound of the invention reduces a cancer cell's viability in the presence of ionizing radiation. In another embodiment of the invention, a radiosensitizing compound of the invention reduces a cancer cell's growth in the presence of ionizing radiation. In still another embodiment of the invention, a radiosensitizing compound of the invention increases the amount, frequency, or severity of DNA damage, including double strand breaks (DSB), that a cancer cell sustains in response to ionizing radiation. In yet another embodiment of the invention, a radio sensitizing compound of the invention reduces a cancer cell's ability to repair DNA damage sustained as a result of ionizing radiation.

In addition, one skilled in the art will recognize that, like ionizing radiation, genotoxic chemotherapy (i.e. doxorubicin, cisplatin, and the like) also induces DNA damage. Therefore a compound of the present invention will also be useful as a chemosensitizing agent. In one embodiment of the invention, a chemosensitizing compound increases the sensitivity of a cancer cell or a tumor to the effects of genotoxic chemotherapy used in the treatment of cancer. In another embodiment of the invention, a chemosensitizing compound of the invention reduces a cancer cell's viability in the presence of genotoxic chemotherapy. In still another embodiment of the invention, a chemosensitizing compound of the invention increases the amount, frequency, or severity of DNA damage, including double strand breaks (DSB), that a cancer cell sustains in response to genotoxic chemotherapy. In yet another embodiment of the invention, a chemosensitizing compound of the invention reduces a cancer cell's ability to repair DNA damage sustained as a result of genotoxic chemotherapy.

The invention comprises a composition comprising a compound of formula (I):

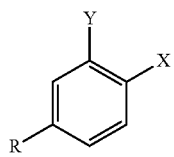

Formula I wherein
Y is $NO_2$, $NR^1{}_3$, CN, CHO, $C(O)R^1$ or $CF_3$;
X is H, F, Cl, Br or I;
R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable analogue, modification, derivative, adduct, salt, pro-drug or solvate thereof, with the proviso that the composition excludes a compound of Formula I, where Y=$NO_2$, R=$C(O)R^1$, and $R^1$=$CH_2CH_3$, where X=F, Cl, Br, or H; Formula I, where Y=$NO_2$, R=$S(O)_2R^1$, and $R^1$=$CH_2CH_3$, where X=Cl, Br, or H; and Formula I, where Y=$NO_2$, R=$P(O)(OH)R^1$, $R^1$=$CH_2CH_3$, where X=H.

In one embodiment, the invention comprises a composition comprising Formula I, where Y=$NO_2$, R=$C(O)R^1$, $R^1$=$CH_2CH_3$, designated Compound 1, and X=I, or an analogue, modification, derivative, adduct, salt, pro-drug or solvate thereof (FIG. 1B (1)).

In another embodiment, the invention comprises a composition comprising Formula I, where Y=$NO_2$, R=$S(O)_2R^1$, $R^1$=$CH_2CH_3$, and X=F or I, designated Compound 2, or an analogue, modification, derivative, adduct, salt, pro-drug or solvate thereof (FIG. 1B (2)).

In still another embodiment, the invention comprises a composition comprising Formula I, where Y=$NO_2$, R=$P(O)(OH)R^1$, $R^1$=$CH_2CH_3$, designated Compound 3, and X=F, Cl, Br, H, or I, or an analogue, modification, derivative, adduct, salt, pro-drug or solvate thereof (FIG. 1B (3)).

When the radiosensitizing compound is a small molecule, a small molecule agonist may be obtained using standard methods known to the skilled artisan.

Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making said libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

II. Methods

The present invention provides a method of increasing the sensitivity of a cancer cell or a tumor to the effects of ionizing radiation used in the treatment of cancer. In another embodiment, the present invention provides a method to reduce a cancer cell's viability in the presence of ionizing radiation used in the treatment of cancer. In still another embodiment, the present invention provides a method to increase the amount, frequency, or severity of DNA damage, including double strand breaks (DSB), that a cancer cell sustains in response to ionizing radiation used in the treatment of cancer. In yet another embodiment, the present invention provides a method to reduce a cancer cell's ability to repair DNA damage sustained as a result of ionizing radiation used in the treatment of cancer.

Genotoxic chemotherapy (e.g. doxorubicin, cisplatin, and the like) causes similar deleterious effects on cancer cells as ionizing radiation, in that both therapeutic modalities kill cancer cells principally by inducing DNA damage. Accordingly, the present invention provides a method of increasing the sensitivity of a cancer cell or a tumor to the effects of genotoxic chemotherapy used in the treatment of cancer. In another embodiment, the present invention provides a method to reduce a cancer cell's viability in the presence of genotoxic chemotherapy used in the treatment of cancer. In still another embodiment, the present invention provides a method to increase the amount, frequency, or severity of DNA damage, including double strand breaks (DSB), that a cancer cell sustains in response to genotoxic chemotherapy used in the treatment of cancer. In yet another embodiment, the present invention provides a method to reduce a cancer cell's ability to repair DNA damage sustained as a result of genotoxic chemotherapy used in the treatment of cancer.

Accordingly, the invention includes a method of increasing the sensitivity of a cancer cell or a tumor to the effects of ionizing radiation used in the treatment of cancer in a subject in need thereof. In one embodiment, the method comprises administering to the subject a therapeutically effective amount of a composition comprising a compound of formula (I):

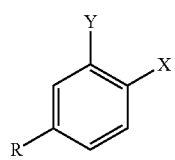

Formula I wherein
Y is $NO_2$, $NR^1_3$, CN, CHO, $C(O)R^1$ or $CF_3$;
X is H, F, Cl, Br or I;
R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable analogue, modification, derivative, adduct, salt, pro-drug or solvate thereof, wherein the compound contacts a cancer cell or tumor in the subject, thereby making the cancer cell or tumor more susceptible to radiation. As used herein, the term "contacting," means that at least one compound of the invention is present in the location of the cell or tumor, particularly in the location of a localized tumor. As disclosed herein, a tumor can be contacted with a compound of the invention, for example, by injecting a solution containing the compound either systemically or into the region of the tumor.

In another embodiment, a method of the invention comprises administering to the subject a therapeutically effective amount of a composition comprising Formula I, $Y=NO_2$, $R=C(O)R^1$, $R^1=CH_2CH_3$, and $X=I$, or an analogue, modification, derivative, adduct, salt, pro-drug or solvate thereof, wherein the composition contacts a cancer cell or tumor in the subject and sensitizes a cancer cell or tumor to ionizing radiation.

In another embodiment, a method of the invention comprises administering to the subject a therapeutically effective amount of a composition comprising Formula I, where $Y=NO_2$, $R=S(O)_2R^1$, $R^1=CH_2CH_3$, and $X=F$ or I, or an analogue, modification, derivative, adduct, salt, pro-drug or solvate thereof, wherein the composition contacts a cancer cell or tumor in the subject and sensitizes a cancer cell or tumor to ionizing radiation.

In another embodiment, a method of the invention comprises administering to the subject a therapeutically effective amount of a composition comprising Formula I, where $Y=NO_2$, $R=P(O)(OH)R^1$, $R^1=CH_2CH_3$, and $X=F$, Cl, Br, H, or I, or an analogue, modification, derivative, adduct, salt, pro-drug or solvate thereof, wherein the composition contacts a cancer cell or tumor in the subject and sensitizes a cancer cell or tumor to ionizing radiation.

The invention also provides a method of sensitizing a tumor in a subject to ionizing radiation by administering, at a site other than the tumor, a composition comprising at least one compound of the invention. Thus, a method of the invention is particularly useful for treating a subject having metastatic lesions that have disseminated from an original tumor site. The invention is useful for treating a subject with a cancer such as a melanoma or any other cancer in which the dissemination of metastatic lesions is common, and provides the additional advantage that recurrence of a tumor is less likely to occur following treatment.

A therapeutically effective dose of a compound or composition of the present invention is one whereby a cancer cell or tumor's growth or proliferation is attenuated as a result of ionizing radiation administered to the subject for the treatment of cancer; the amount, frequency, or severity of DNA damage, including double strand breaks (DSB), that a cancer cell sustains in response to ionizing radiation used in the treatment of cancer is increased; a cancer cell's ability to repair DNA damage sustained as a result of ionizing radiation used in the treatment of cancer is reduced; a cancer cell is induced to undergo apoptosis; or a lower dose of ionizing radiation is made more effective by using a radiosensitizer of the present invention with ionizing radiation for treating a cancer or tumor in a subject. In another embodiment of the invention, the frequency or severity of symptoms associated with the growth and proliferation of a cancer cell are attenuated.

In one embodiment of the invention, the subject is a mammal. In another embodiment of the invention, the subject is a human. The subject may be diagnosed with a neoplastic disease, a cancer, a malignancy, or a tumor. The cancer or tumor may be localized, diffuse, or metastatic. In one embodiment, the subject has glioblastoma multiforme. In another embodiment, the subject has small cell lung carcinoma. In still another embodiment, the subject has colorectal cancer.

The methods of the present invention can be used in combination with other treatment regimens, including virostatic and virotoxic agents, antibiotic agents, antifungal agents, anti-inflammatory agents (steroidal and non-steroidal), antidepressants, anxiolytics, pain management agents, (acetaminophen, aspirin, ibuprofen, opiates (including morphine, hydrocodone, codeine, fentanyl, methadone), steroids (including prednisone and dexamethasone), and antidepressants (including gabapentin, amitriptyline, imipramine, doxepin) antihistamines, antitussives, muscle relaxants, brondhodilaters, beta-agonists, anticholinergics, corticosteroids, mast cell stabilizers, leukotriene modifiers, methylxanthines, nucleic acid based therapeutic agents, as well as combination therapies, and the like. The compounds of the present invention may be administered before, during, after, or throughout administration of any therapeutic agents used in the treatment of a subject's disease or disorder.

The invention can also be used in combination with other treatment modalities, such as chemotherapy, cryotherapy, hyperthermia, radiation therapy, and the like. Chemotherapy and radiation are commonly used as components of a combined modality treatment, and the choice of chemotherapeutic agent(s) and type and course of radiation therapy is generally governed by the characteristics of the individual cancer and the response of the individual. They can also be combined with both methods of treatment in the same course of therapy. Accordingly, the present invention encompasses combinations of the methods discussed above. Accordingly, the invention includes methods for suppressing tumor growth in an individual comprising the following steps, in any order:
a) administering to the individual an effective amount of a radiosensitizing compound of the invention; and b) administering an effective amount of an appropriate course of radiation therapy to the individual. The method may further comprise the step of c) administering to the individual an additional dose of a radiosensitizing compound of the invention or radiation as necessary to treat the individual's cancer. The method may further comprise time delays after any one of steps a), b) and c). A time delay interval may be days, weeks or months.

Pharmaceutical Compositions

The compounds disclosed herein, as well as analogues, modifications, derivatives, adducts, salts, pro-drugs or solvates thereof, may be formulated and administered to a subject diagnosed with cancer for the purpose of rendering a cancer cell susceptible to chemotherapeutic and radiation therapy.

The invention encompasses the preparation and use of pharmaceutical compositions comprising a compound useful for treatment of the diseases disclosed herein as an active ingredient. The term "pharmaceutical composition" refers to a mixture of a compound of formula (I) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration, including sub-lingual administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration, a skilled artisan can readily determine the appropriate dosage for each subject based on methods known in the art. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

III. Cell-Based High Throughput Screening of Test Compounds

A test compound useful in the present invention is a potential radiosensitizing molecule and may be a peptide, a nucleic acid, a small molecule, or other drug that renders a cancer cell or tumor more susceptible to the effects of ionizing radiation administered to a subject as part of a therapeutic treatment for cancer. Test molecules may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145).

Examples of methods for the synthesis of molecular libraries may be found in the art, for example, in: DeWitt et al., 1993, Proc. Natl. Acad. Sci. USA 90:6909-6913; Erb et al., 1994, Proc. Natl. Acad. Sci. USA 91:11422-11426; Zuckermann et al., 1994, J. Med. Chem. 37:2678-2685; Cho et al., 1992, Science 261:1303-1305; Carell et al., 1994, Angew. Chem. Int. Ed. Engl. 33:2059-2061; Carell et al., 1994, Angew. Chem. Int. Ed. Engl. 33:2061-2064; and Gallop et al., 1994, J. Med. Chem. 37:1233-1251.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869), or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J Mol. Biol. 222:301-310).

The resulting libraries of candidate molecules may be screened to determine their efficacy as radiosensitizers using any technique well known in the art. Such techniques include, but are not limited to, high-throughput bioassays, such as binding assays or activity based assays; structural analysis such as X-ray crystallography; drug fragment-based analysis, including binding assays; computational analysis (e.g. Target Infomatics Platform, Eidogen; Passadena, Calif.); animal-based, tissue-based, or cell-based assays, to determine a molecule's efficacy as a radiosensitizer.

By way of several experimental examples presented herein, the present invention encompasses a novel cell-based high throughput assay for screening test compounds for radiosensitizing effects. In another embodiment, the present invention further comprises a cell-based high throughput assay for screening test compounds for sensitizing a cancer cell or tumor to the effects of a chemotherapeutic agent used in the treatment of cancer.

IV. Kits

The invention also includes a kit comprising at least one compound of the invention and instructional material which describes, for instance, administering a compound to a subject as a therapeutic treatment as described elsewhere herein.

In one embodiment, a kit may comprise instructional material, an optional applicator, and a therapeutically effective amount of a composition comprising a compound of formula (I):

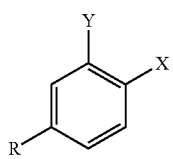

Formula I wherein
Y is $NO_2$, $NR^1{}_3$, CN, CHO, $C(O)R^1$ or $CF_3$;
X is H, F, Cl, Br or I;

R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable analogue, modification, derivative, adduct, salt, pro-drug or solvate thereof, with the proviso that the composition excludes a compound of:
Formula I, where Y=$NO_2$, R=$C(O)R^1$, and $R^1$=$CH_2CH_3$, designated Compound 1, where X=F, Cl, Br, or H;
Formula I, where Y=$NO_2$, R=$S(O)_2R^1$, and $R^1$=$CH_2CH_3$, designated Compound 2, where X=Cl, Br, or H; and
Formula I, where Y=$NO_2$, R=$P(O)(OH)R^1$, $R^1$=$CH_2CH_3$, designated Compound 3, where X=H.

In another embodiment, a kit of the invention may comprise a therapeutically effective amount of a composition comprising Formula I, Y=$NO_2$, R=$C(O)R^1$, $R^1$=$CH_2CH_3$, and X=I, or an analogue, modification, derivative, adduct, salt, pro-drug or solvate thereof, instructional material, and, optionally, an applicator.

In another embodiment, a kit of the invention may comprise a therapeutically effective amount of a composition comprising Formula I, where Y=$NO_2$, R=$S(O)_2R^1$, $R^1$=$CH_2CH_3$, and X=F or I, or an analogue, modification, derivative, adduct, salt, pro-drug or solvate thereof, instructional material, and, optionally, an applicator.

In another embodiment, a kit of the invention may comprise a therapeutically effective amount of a composition comprising Formula I, where Y=$NO_2$, R=$P(O)(OH)R^1$, $R^1$=$CH_2CH_3$, and X=F, Cl, Br, H, or I, or an analogue, modification, derivative, adduct, salt, pro-drug or solvate thereof, instructional material, and, optionally, an applicator.

In an embodiment, this kit further comprises a (preferably sterile) pharmaceutically acceptable carrier suitable for dissolving or suspending the therapeutic composition, comprising a radiosensitizer of the invention, for instance, prior to administering the molecule to a subject.

In another embodiment, a kit of the invention comprises materials and instructions for high-throughput screening of a peptide, a nucleic acid, a small molecule, or other drug for properties that renders a cancer cell or tumor more susceptible to the effects of ionizing radiation or chemotherapeutic agents administered to a subject as part of a treatment for cancer.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Chemicals A library consisting of 10,000 compounds was obtained from Nanosyn, Inc (Menlo Park, Calif.). 87% of these compounds conform to 4 Lipinski criteria and 98% to 3 Lipinski criteria, suggesting that they have desirable pharmacologic properties (Lipinski et al., 2001, Adv. Drug Deliv. Rev. 46:3-26). NS-123 (500 mg) was synthesized both via a contract from Exclusive Chemistry, LTD (Moscow, Russia) and as a generous gift from Dr. Robert Mach (Washington University, St. Louis, Mo.). Chemical structure and purity of the synthesized product was confirmed by NMR and mass spectroscopy.

Other compounds, as disclosed herein, were either obtained from Sigma-Aldrich (St. Louis, Mo.), or ACROS Organics (Morris Plains, N.J.) or synthesize using standard methods known in the art.

Synthesis of Compound 2

Figure 2:
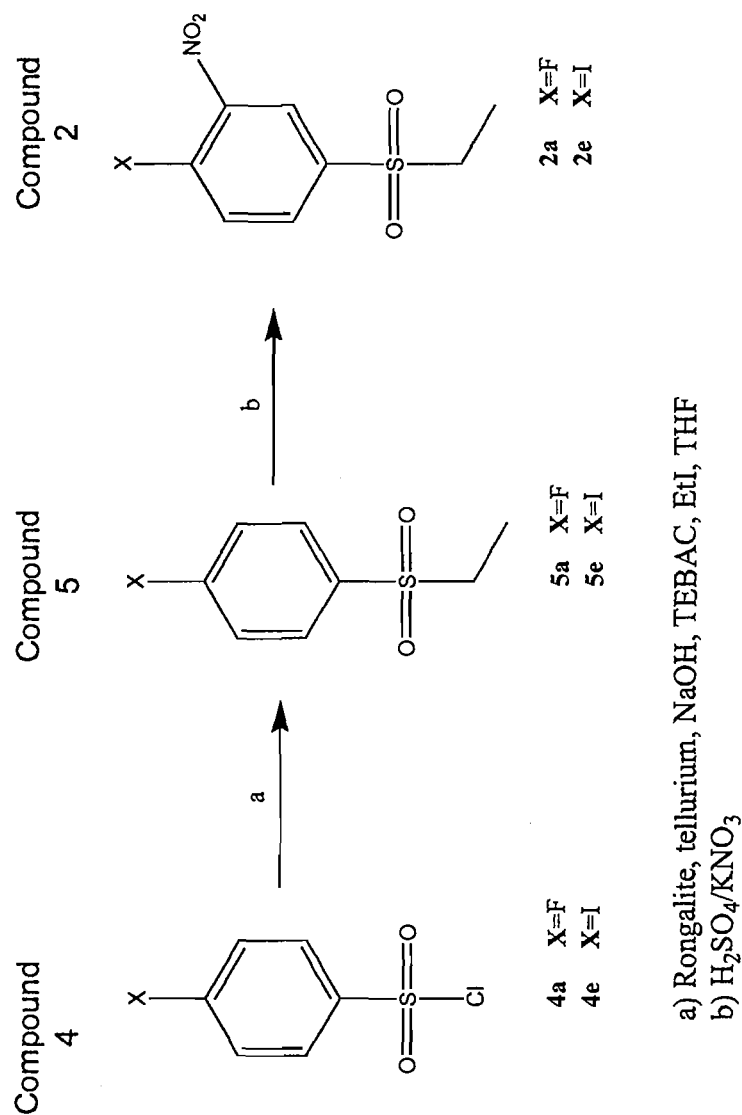
FIG. 2 is a series of images depicting the synthesis of Formula I, where Y=$NO_2$, R=$S(O)2R^1$, and $R_1$=$CH_2CH_3$ (Compound 2) where X=F (Compound 2a) or I (Compound 2e) starting from Compound 4, where X=F (Compound 4a) or I (Compound 4e) and proceeding through intermediary Compound 5 where X=F (Compound 5a) or (Compound 5e).

A schematic illustration of Formula I, where Y=$NO_2$, R=$S(O)_2R^1$, $R^1$=$CH_2CH_3$ (Compound 2) is depicted in FIG. 1B and FIG. 2. The synthesis of Compound 2 is illustrated in FIG. 2 (Suzuki et al., 1985, Chem. Lett. 225-228; Suzuki et al., 1988, Chem. Lett. 727-728; Kon-I et al., 2006, U.S. Patent Application No. 2006094750.

Apparatus

Melting points were determined with a Mel-Temp electrothermal apparatus and are uncorrected. The $^1H$ NMR spectra were recorded with a 400 MHz Bruker NMR spectrophotometer with TMS as internal standard and $CDCl_3$ as solvent. The Mass spectra were recorded with a Varian 1200 Triple Ouadrupole instrument using electrospray ionization (ESI) technique. Column chromatography was conducted using Merck silica gel, grade 9385, 230-400 mesh, 60 Å. HPLC was conducted using C18 column, elution solution of water/acetonitrile/formic acid and Hitachi Elite LaChrom with UV detection. Elemental Analyses were performed by Galbraith Laboratories, Knoxville, Tenn. and observed values were within +/−0.4% of theoretical values.

1-(Ethylsulfonyl)-4-fluorobenzene (Compound 5a)

A reddish solution of sodium telluride, prepared by heating a mixture of powdered tellurium (10 mmol, 1.28 g), Rongalite (also known as formaldehydedesulfoxylate dihydrate) (50 mmol, 7.71 g) and 1 M aqueous sodium hydroxide (25 ml), was added dropwise to a stirred solution of p-fluoro-sulfonyl chloride (10 mmol, 1.94 g) and triethylbenzylammonium chloride (TEBAC) (0.1 mmol, 0.23 g) in THF (30 ml) at room temperature under nitrogen. An instantaneous reaction occurred and the color of the reaction mixture changed to deep black. After 5 minutes while stirring, iodoethane (50 mmol, 4 ml) in THF (3 ml) was added and the resulting mixture was kept at 90° C. for 5 hours. After cooling, the solvent was removed under reduced pressure and the residue was treated with aqueous ammonium chloride and benzene. Organic phase was separated, dried over sodium sulfate, and the solvent evaporated. The residue was purified by column chromatography (hexane/ethylacetate 1:1) to give a white solid which was crystallized from chloroform and hexane. HPLC indicated 94% purity, mp 39-40° C., (0.30 g, 16% yield). $^1H$ NMR (CDCl3): 1.6 (t, 3H, $CH_3$), 3.23 (q, 2H, $CH_2$), 7.27 (m, 2H, Ar—H), 7.94 (m, 2H, Ar—H); MS: 189 $M^+$. Elemental Analysis (C, H, F, S) for $C_8H_9FO_2S$; calculated C, 51.05; H, 4.82; F, 10.09; S, 17.04. found C, 51.07; H, 4.67; F, 10.36; S, 16.85.

1-(Ethylsulfonyl)-4-iodobenzene (Compound 5e)

Compound 5e was prepared in analogy to Compound 5a, starting from pipsyl chloride (10 mmol, 3.02 g). A white solid was crystallized from ethyl acetate and hexane. HPLC indicated 100% purity, mp 78-79° C., (0.60 g, 20% yield). $^1H$ NMR (CDCl$_3$): 1.28 (t, 3H, $CH_3$), 3.12 (q, 2H, $CH_2$), 7.63 (d, 2H, Ar—H), 7.96 (d, 2H, Ar—H); MS: 296 $M^+$. Elemental Analysis (C, H, I, S) for $C_8H_9IO_2S \cdot 0.2C_6H_{14} \cdot 0.1H_2O$; calculated C, 35.06; H, 3.83; I, 40.26; S, 10.17. found C, 35.04; H, 3.41; I, 40.32; S, 9.74.

4-(Ethylsulfonyl)-1-fluoro-2-nitrobenzene (Formula I, where R=$S(O)_2R_1$, $R_1$=$CH_2CH_3$, and X=F; Compound 2a)

To a solution of 1-(ethylsulfonyl)-4-fluorobenzene (1.36 mmol, 0.257 g) in sulfuric acid (1.32 ml) was added potassium nitrate (0.243 g) at 80° C. The mixture was stirred at 90° C. for 2 hours. Ice water (5 ml) was added and the mixture was extracted with ethyl acetate (25 ml) and washed with water (20 ml) and brine (10 ml). The organic extracts were combined and dried over sodium sulfate and concentrated. The residue was purified by column chromatography (hexane/ethylacetate 1:3) to give a light yellow solid which was crystallized from methanol. HPLC indicated 98% purity, mp 128-131° C., (0.21 g, 66% yield). $^1H$ NMR (CDCl$_3$): 1.35 (t, 3H, $CH_3$), 3.21 (q, 2H, $CH_2$), 7.55 (t, 1H, Ar—H), 8.21 (m, 1H, Ar—H), 8.64 (d, 1H, Ar—H); MS: 229 $M^-$. Elemental Analysis (C, H, N, F, S) for $C_8H_8FNO_4S$; calculated C, 41.20; H, 3.46; N, 6.01; F, 8.15; S, 13.75. found C, 41.31; H, 3.35; N, 5.85; F, 8.17; S, 13.53.

4-(Ethylsulfonyl)-1-iodo-2-nitrobenzene (Formula I, where R=$S(O)_2R_1$, $R_1$=$CH_2CH_3$, and X=I; Compound 2e)

Compound 2e was prepared in analogy to Compound 2a, starting from 1-(ethylsulfonyl)-4-iodobenzene (0.34 mmol, 0.10 g) to give a light yellow solid which was crystallized from ethyl acetate and hexane. HPLC indicated 98% purity, mp 124-126° C., (0.052 g, 45% yield). $^1H$ NMR (CDCl$_3$): 1.35 (t, 3H, $CH_3$), 3.22 (q, 2H, $CH_2$), 7.77 (dd, 1H, Ar—H), 8.31 (d, 1H, Ar—H), 8.34 (d, 1H, Ar—H); MS: 338.9 M Elemental Analysis (C, H, N, I, S) for $C_8H_8INO_4S$; calculated C, 28.17; H, 2.36; N, 4.11; I, 37.20; S, 9.40. found C, 28.25; H, 2.25; N, 3.99; I, 37.39; S, 9.18.

Cell Culture

All cell lines (American Type Culture Collection, Manassas, Va.) were incubated at 37° C. with 5% $CO_2$. U251 glioma, HT-29 colorectal cancer, and A549 non-small cell lung cancer cells were grown in RPMI 1640, McCoy 5A, and Ham's/F12 medium respectively, supplemented with 10% fetal bovine serum, L-glutamine, and penicillin/streptomycin. Nontransformed human astrocytes (NHA, Cambrex, La Jolla, Calif.) were cultured according to the manufacturer's instructions in astrocyte basal medium (ABM; Cambrex La Jolla, Calif.) supplemented with ascorbic acid, recombinant human epidermal growth factor (rhEGF), GA-1000, insulin, L-glutamine, and 3% FBS. In all of the tissue culture experiments, NS-123 was readily dissolved in DMSO and was added to cells such that the maximum concentration of DMSO was 0.1% v/v.

Chemical Library Screen

Six hundred U251 cells were plated per well in 96 well plates. Cells in each well were then treated with a different compound from the Nanosyn library for 8 hours at 2.5 μM concentration. Treatment was performed with paired 96-well plates; one plate was exposed to 4 Gy and the other plate was an unirradiated control. One hour after irradiation, the medium was replaced with fresh medium alone. Four days later, the MTS assay was used to evaluate cell survival. Absorbance was measured at 490 nm with a microplate reader (Sprectramax, Molecular Devices, Sunnyvale, Calif.). Radiosensitivity factors (RSF) were calculated according to the following formula for each compound tested with the assay:

$$RSF = \frac{\text{Optical density reading with radiaton}}{\text{Optical density reading without radiation}}$$

Survival Assays

Clonogenic survival assays were performed as described by Koumenis, et al., 2002, (Mol. Cell Biol. 22:7405-16), which reference is incorporated herein in its entirety. U251, HT-29, or A549 cells were plated at different densities in triplicate, treated with NS-123 or DMSO (alone) and irradiated 4, 8, or 12 hours later with a range of doses using $^{137}$Cs γ-rays at a dose rate of ~4 Gy/minute (min). One hour after irradiation, the medium was replaced with fresh medium without NS-123 or DMSO. The cells were fixed 7-14 days after IR and stained with crystal violet. Colonies greater than 50 cells were then counted and normalized against the non-irradiated controls for each treatment. Since normal human cells do not grow clonogenically, MTS assays were used to assess survival. Previous studies demonstrated that MTS assays, when performed on sub-confluent cultures of tumor cells for >5 days following IR, yield results that are comparable to those of clonogenic survival assays (Naczki and Koumenis, unpublished results). NHA cells were plated in 24-well plates in quadruplicate at equal density, treated with equal volumes of NS-123 or DMSO (alone) and irradiated as described above. One hour after irradiation, the medium was replaced with fresh ABM. Five days later, the MTS assay was used to evaluate cell survival as above.

Immunoblotting

Following treatments, whole cell and nuclear extracts were prepared. Equal lysate volumes were loaded on 15% and 12% SDS-PAGE gels to assay for γ-H2AX and P-CHK2 proteins, respectively. To assay for P-ATM and P-DNA-PKcs protein, 30-50 μg of nuclear protein were diluted with an equal volume of 2×SDS and resolved with 6% SDS-PAGE gels. Proteins were transferred to polyvinylidene difluoride (PVDF) membranes and then incubated with either anti-γ-H2AX antibody (1:5000; Upstate, Charlottesville, Va.), anti-P-CHK2 antibody (1:1000; Cell Signaling, Beverly, Mass.), anti-phospho-ATM (pSer$^{1981}$) antibody (1:300 Calbiomchem, San Diego, Calif.), or anti-phospho-DNA-PKcs (T2609) antibody (1:500; Abcam, Cambridge, Mass.). To confirm equivalent loading and protein transfer, membranes were probed with mouse anti-human β-actin monoclonal antibody (Sigma) or anti-DNA-PKcs monoclonal antibody (25-4 at 1:5000; Neo-Markers, Fremont, Calif.). All membranes were then incubated with horseradish peroxidase-conjugated anti-mouse or anti-rabbit secondary antibodies (Santa Cruz Biotechnology). Immunoreactive bands were detected using ECL Plus chemiluminescence (Amersham Biosciences).

Double Strand Break (DSB) Measurement Using Pulsed Field Gel Electrophoresis (PFGE) and Number Average Length Analysis (NALA)

Cells were treated with 30 μM NS-123 or DMSO alone. Four hours later, the cells were either sham-irradiated, or irradiated with 4 Gy of $^{137}$Cs γ-rays (Radiation Facility, Brody School of Medicine, ECU) at the dose rate of 0.57 Gy/min and placed immediately at 37° C. in fresh medium without NS-123 and harvested at different repair times up to 24 hours. No significant changes in the percentage of dead cells were detected by trypan blue exclusion as a result of irradiation. After mixing of cells into low melting point agarose (Biorad, Hercules Calif.) plugs (~200,000 cells/plug), each plug was placed in 10 mL of TE buffer for 1 hour, followed by treatment with 1 mg/mL proteinase K (Promega) for 2 hours, and then placed at 37° C. for lysis. Proteinase K solution was replaced every 24 hours along with a daily 0.5% reduction in N-lauroylsarcosine concentration. Lysed cell plugs were washed in NTE buffer (150 mM NaCl, 10 mM Tris-HCl, 0.1 mM EDTA, pH 8.0 supplemented with 40 ng/ml phenylmethylsulphonyl fluoride-PMSF) and stored in fresh TE buffer. For the AscI (New England Biolabs, Beverly, Mass.) restriction enzyme treatment, plugs were washed using 1 mL AscI reaction buffer (20 mM Tris-acetate, 10 mM magnesium acetate and 50 mM potassium acetate, pH 7.9) for 1 hour, replaced with fresh buffer every 20 minutes and then incubated for 24 hours at 4° C. Plugs were incubated for 1 hour on ice, and then moved to 37° C. for 16 hours. After incubation, AscI enzyme solution was removed and replaced with 1 mL of ice-cold native stop solution (70 mM HEPES-KOH, 100 mM KCl and 100 mM EDTA, pH 7.6). Plugs were washed with TE buffer (six times, 1 hour each), and then equilibrated into 0.5×TBE (45 mM Tris base, 45 mM boric acid and 1 mM Na$_2$-EDTA, pH 7.8). Samples and molecular length standards were electrophoresed in a 0.85% neutral gel prepared in 0.25×TBE in a BioRad CHEF DR-II apparatus and electrophoresed using a dual pulsed field gel electrophoresis (PFGE) pulsing regime, optimized for separation of DNA fragments ranging from 5.7 Mbp-9.4 kbp. Gels were stained with ethidium bromide (1 μg/mL) for 1 hour, destained overnight, and an electronic image was obtained using a FluorChem™ 8800 imaging system (Alpha Innotech, San Leandro, Calif.). Images were processed using QuantiScan (BioSoft, Cambridge, UK) and a densitogram was obtained for each gel lane. A DNA dispersion curve relating DNA length to electrophoretic mobility, based on all length standards was determined from an analytical mobility function as previously described using number average length analysis (NALA) (Seo, et al., 2005, Clin. Cancer Res. 11:7499-507).

Zebrafish (ZF) Maintenance, Embryo Irradiation and Drug Exposure

ZF were raised in accordance with previously established protocols (McAleer, et al., 2005, J. Radiat. Oncol. Biol. Phys. 61:10-3) at the University of Pennsylvania School of Medicine. Embryos were maintained at 30° C. after transplantation procedures. The age of embryos is indicated as the hours post-fertilization (hpf) and days post-fertilization (dpf) for all experimental data shown. Embryos were either irradiated with 10 Gy or sham-irradiation as previously described (McAleer, et al., 2005, J. Radiat. Oncol. Biol. Phys. 61:10-3) immediately after photography at 24 hpf. Selected embryos were incubated with NS-123 at a concentration of 30 μM for 14 hours before either irradiation or sham-irradiation.

U251 Xenograft ZF Model

U251 cells were stably transfected with a RFP construct (pDsRed2-C 1; Clontech, Palo Alto, Calif.). Using a Nanoject II microinjector (Drummond Scientific, Broomall, Pa.) 1-100 cells were transplanted into each ZF embryo still in the chorion, from the high stage of their development (approximately 3.5 hpf) to the oblong-sphere stage (approximately 4.5 hpf). The transplantation site was localized either to the blastodisc approximately halfway between the margin and the animal pole or the center of the embryonic yolk sac. Morphological analysis was performed as previously described (Geiger, et al., 2006, Cancer Res. 66:8172-81). Transplanted embryos were examined under a 100× PlanNeofluor objective mounted on a Nikon TE-200 epifluorescence microscope. Images of embryos bearing RFP-positive cells were captured with a Hammamatsu CCD camera controlled with IP LabSpectrum v2.0.1 software (Scanalytics, Inc., Rockville, Md.). Image analysis and pseudocoloring was performed with Kodak Molecular Imaging software v. 4.0.5

(Kodak, Rochester, N.Y.). Two images were taken in the same focal plane in bright field and in transmitted light passing through RFP filters, and processed by Adobe Photoshop CS2 (Adobe, San Jose, Calif.).

Nu/Nu Mouse Maintenance and NS-123 Toxicity Evaluation

Female nu/nu (nude) mice (6-8 weeks old; Charles River, Wilmington, Mass.) were maintained at the WFUSM animal facility under conditions approved by the Animal Care and Use Committee. NS-123 in DMSO was mixed with 30% propylene glycol (DMSO concentration<1%) and administered via an i.p. injection at a dose of 50 mg/kg to three mice on three consecutive days. The mice were monitored over 30 days for signs of drug-related toxicity, lethality, and weight loss. Mice were euthanized by $CO_2$ asphyxiation and necropsy was performed by a veterinary pathologist. The heart, lung, liver, spleen, kidney, brain, salivary gland, gastrointestinal tract, ovary, uterus, adrenal gland, and thyroid gland were preserved in 10% neutral buffered formalin for at least 48 hours. The tissues were embedded in paraffin, processed routinely for histology, cut at 4-6 microns, stained with hematoxylin and eosin and examined by light microscopy.

U251 Xenograft Mouse Model

U251 cells ($5 \times 10^6$) were suspended in 0.1 mL of PBS and then injected into the flanks of nu/nu female nude mice. After tumors formed ($45 \pm 10$ mm$^3$), mice were randomly assigned into one of four groups: DMSO+Sham IR, DMSO+5 Gy IR, NS-123+Sham IR, and NS-123+5 Gy IR. NS-123 was administered as described above. Groups not receiving NS-123 were treated with the same volume of DMSO alone dissolved in 30% propylene glycol. Mouse flanks were irradiated 4 hours following the second injection with 5 Gy (Precision X-Ray, Inc, North Branford, Conn.) given as one fraction or Sham IR. Tumor volumes were measured every other day based on the formula:

Volume=length$^2$×width where length was always the longest dimension.

Data are presented as average relative tumor volume (RTV), where:

RTV[Day$_x$]=Volume[Day$_x$]/Volume[Day$_0$]

The measurement of tumor regrowth was calculated by the time needed to grow to 10× the treatment volume. As per Seo et al, 2005, (Clin. Cancer Res. 11:7499-507), the in vivo radiosensitizer enhancement ratio was defined as the ratio:

$T_{NS-123+IR}/T_{DMSO+IR}$ where T is tumor regrowth delay (days)

The results of the experiments presented in this Example are now described.

Example 1

Initial Radiosensitizer Screen and Identification of NS-123

The small chemical compound chemical library (Nanosyn, Inc.) was replicated in a 96-well format and compounds were dissolved in DMSO at a concentration of 2 µM. Using the U251 glioma cell line, the radiosensitizing capability of 870 compounds was initially assayed within the library. The assay was optimized in terms of the number of cells, radiation dose used, and the number of days incubated so that a decrease in survival could be assessed. NS-123 exhibited the highest average RSF of 4.62 among the 870 compounds and was selected for further investigation. The structure for NS-123 is shown in FIG. 1A. The structure of three novel radiosensitizing compounds is depicted in FIG. 1B.

Example 2

NS-123 Radiosensitizes U251 Glioma Tumor Cells

Figure 3:
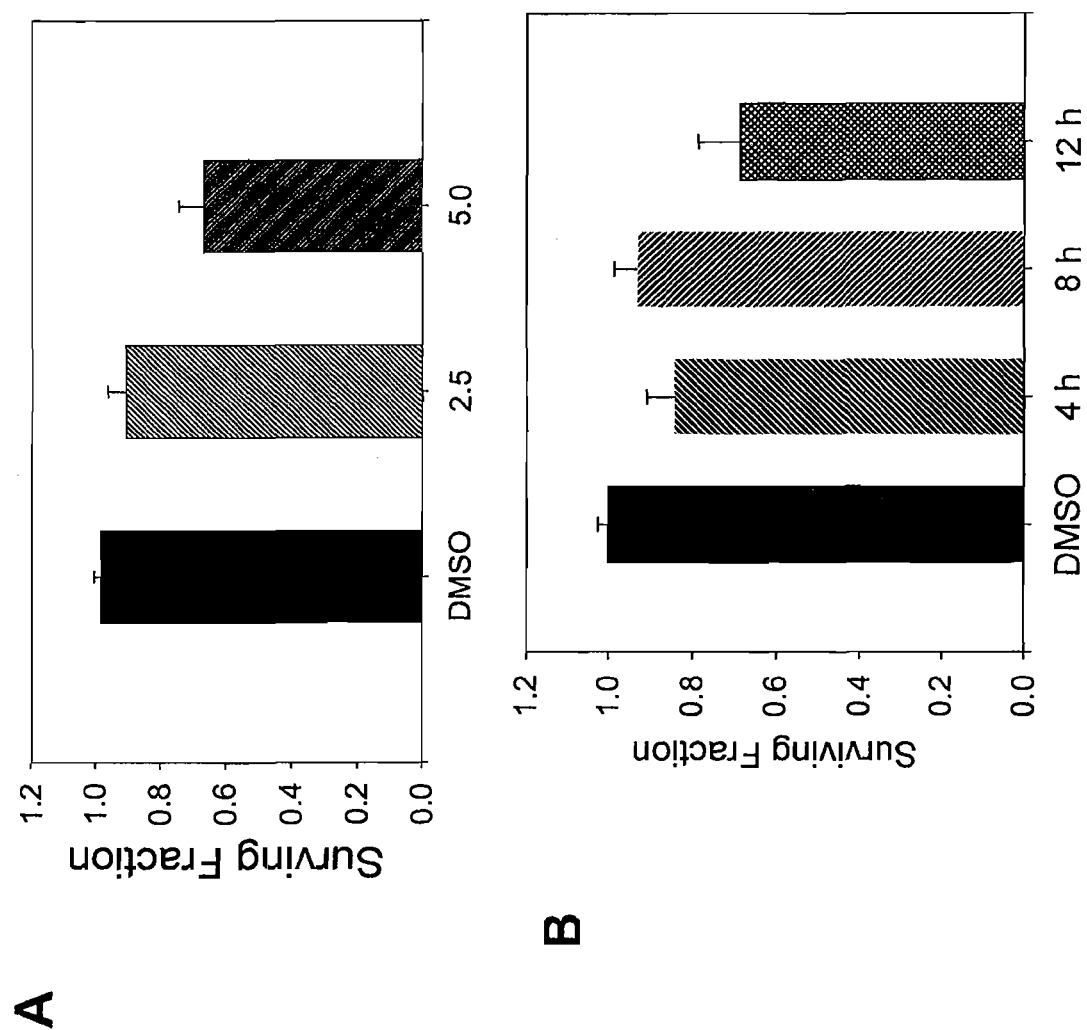
FIG. 3, comprising FIG. 3A

The effects of µM doses of NS-123 on clonogenic survival of U251 cells were first determined without ionizing radiation (IR). As shown in FIG. 3A, treatment with 2.5 µM NS-123 for 12 hours did not cause any significant decrease in survival, which is in agreement with the results from the screening assay. Treatment with a 5 µM dose for 12 hours caused a modest (30%), but statistically significant decrease in survival. In time-response experiments, a 5 µM dose of NS-123 did not induce any significant loss of viability unless it was administered for 12 hours as seen in FIG. 3B.

Figure 4:
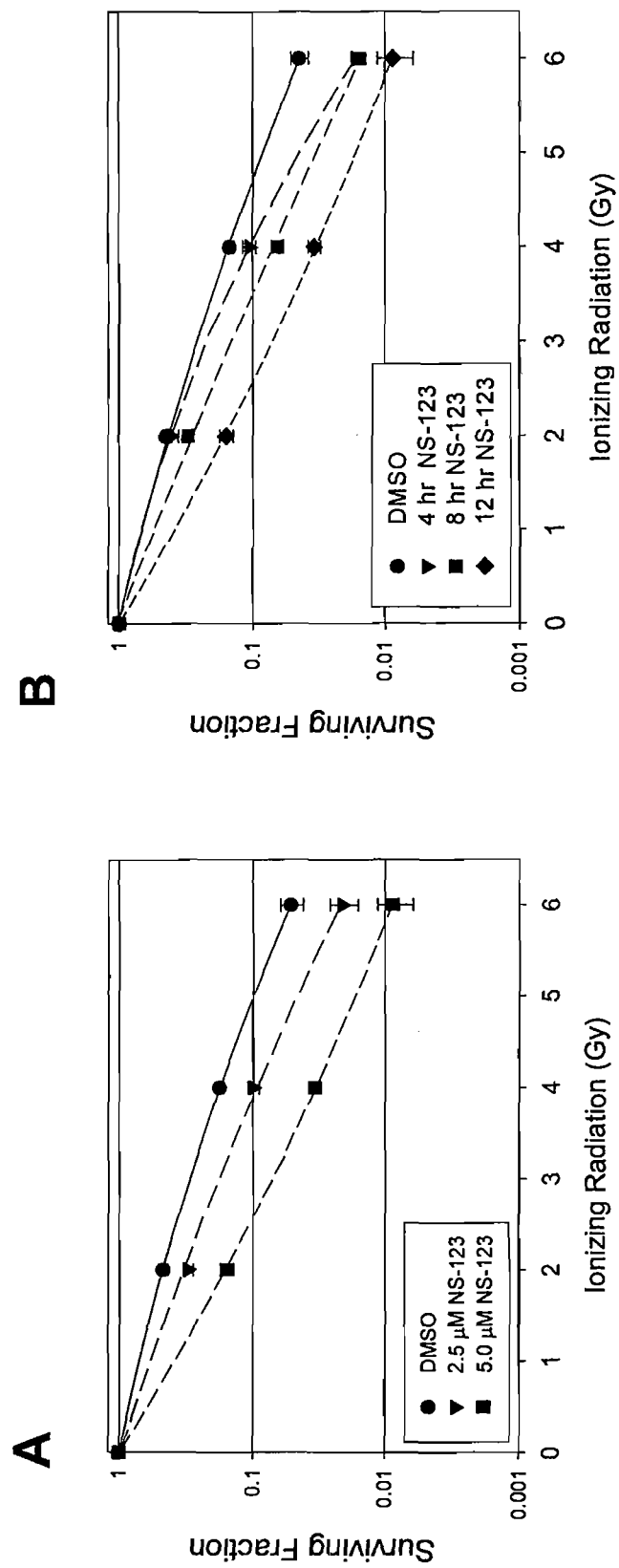
FIG. 4, comprising
Figure 4:
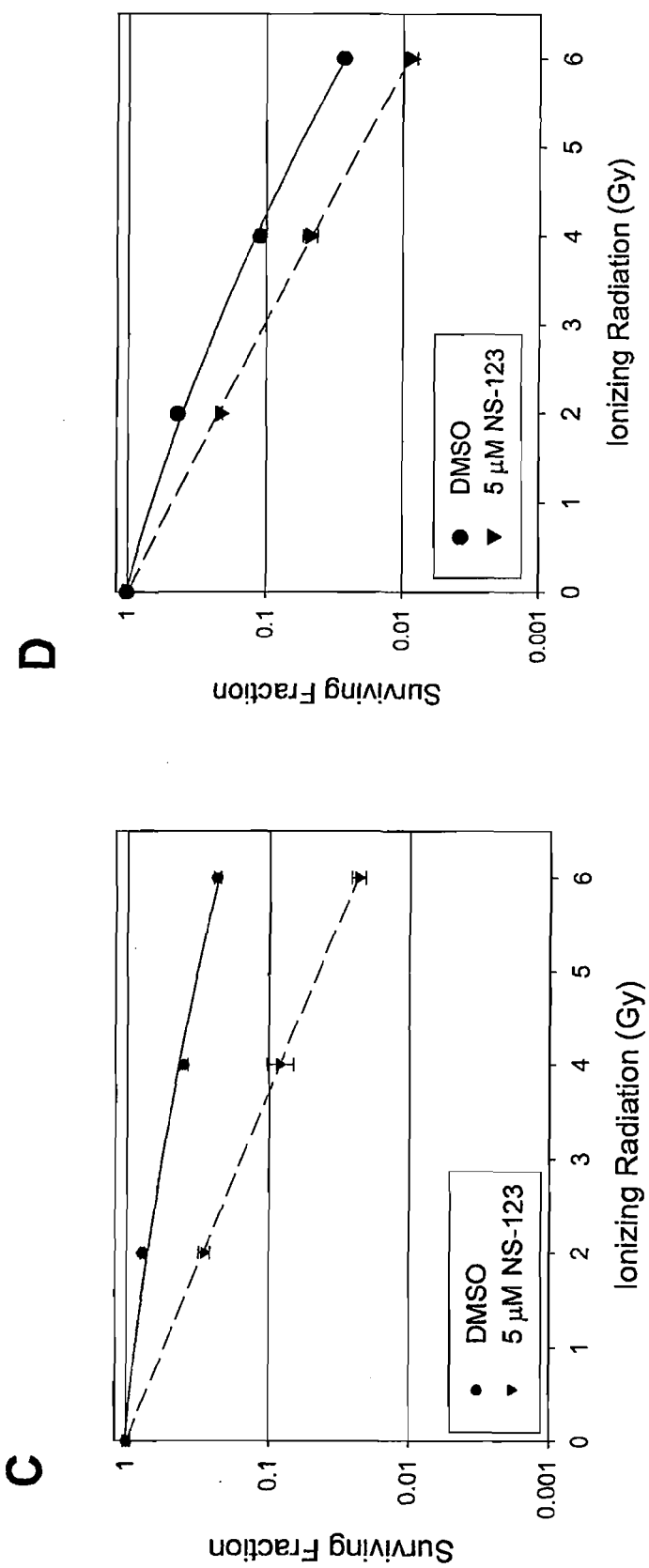

Next, the dose-dependent radiosensitizing effects of NS-123 (2.5 µM and 5.0 µM concentration) in U251 cells was determined (FIG. 4A). Radiosensitization was evident at 2.5 µM, a dose at which NS-123 did not cause any significant loss of viability, and at the radiobiologically-relevant IR dose of 2 Gy used in fractionated radiation schemes. Therefore, NS-123 can act as a true radiosensitizer at low µM concentrations. Corresponding Dose Enhancement Ratios (DER) at 0.1 survival were: 1.3 (2.5 µM NS-123) and 2.0 (5.0 µM NS-123). The time-dependent radiosensitizing effects of 5.0 µM NS-123 in U251 cells was then investigated. As shown in FIG. 4B, NS-123 induced a dose-dependent increase in radiosensitization. Corresponding DER at 0.1 survival were: 1.2 (4 hour preincubation with NS-123), 1.4 (8 hour) and 1.9 (12 hour).

Example 3

NS-123 Radiosensitizes HT-29 Colorectal Cancer Cells and A549 Lung Tumor Cells

To exclude the possibility that the radiosensitizing effect of NS-123 was specific to a single cell line, the radiosensitizing effect of NS-123 was tested on additional cell lines of different tissue origin. Clonogenic survival assays were performed. Pretreatment of HT-29 colorectal cancer cells and A549 non-small cell lung cancer cells with NS-123 induced significant radiosensitization in both cell lines (FIGS. 4C and 4D), with DER values at 0.1 survival of 3.0 and 1.4, respectively. These results show that the radiosensitization of NS-123 is not restricted to only one cell line.

Example 4

NS-123 Does Not Radiosensitize Normal Cells

Figure 5:
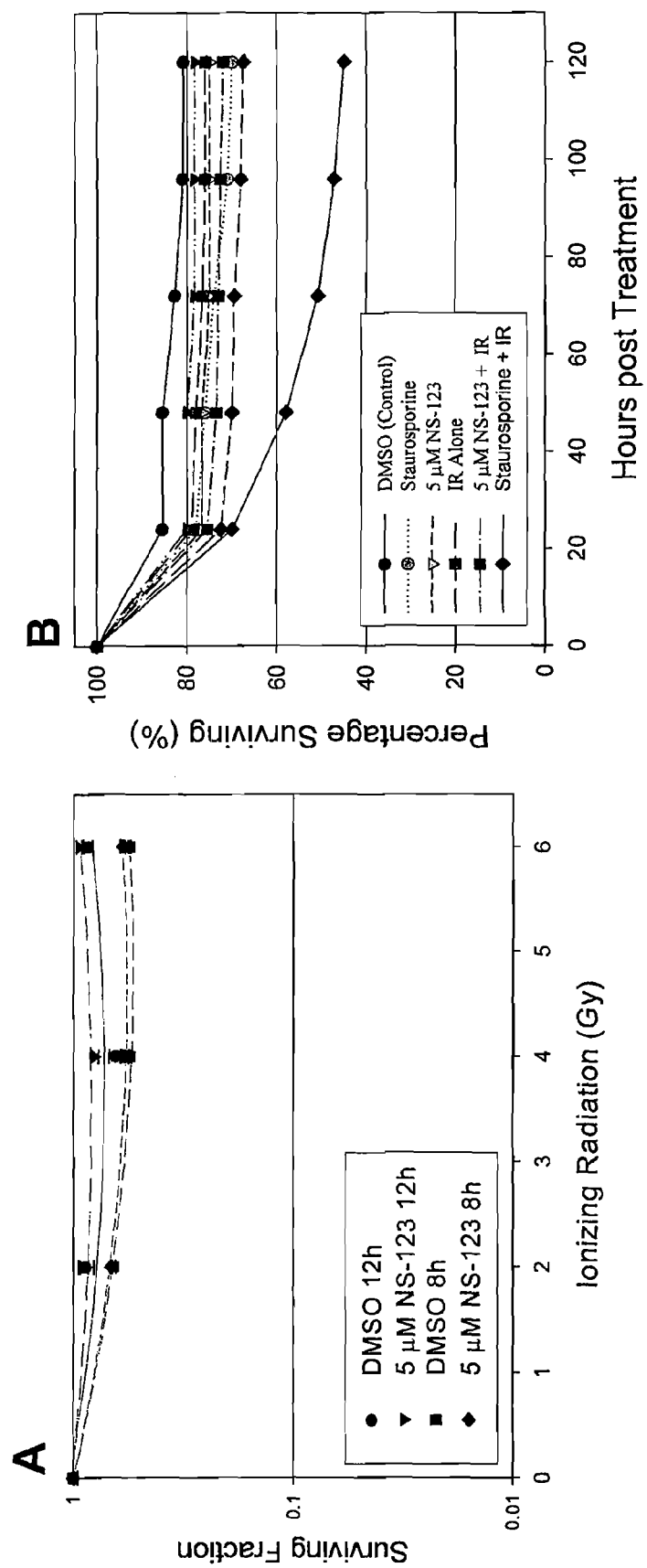
FIG. 5, comprising
Figure 5:
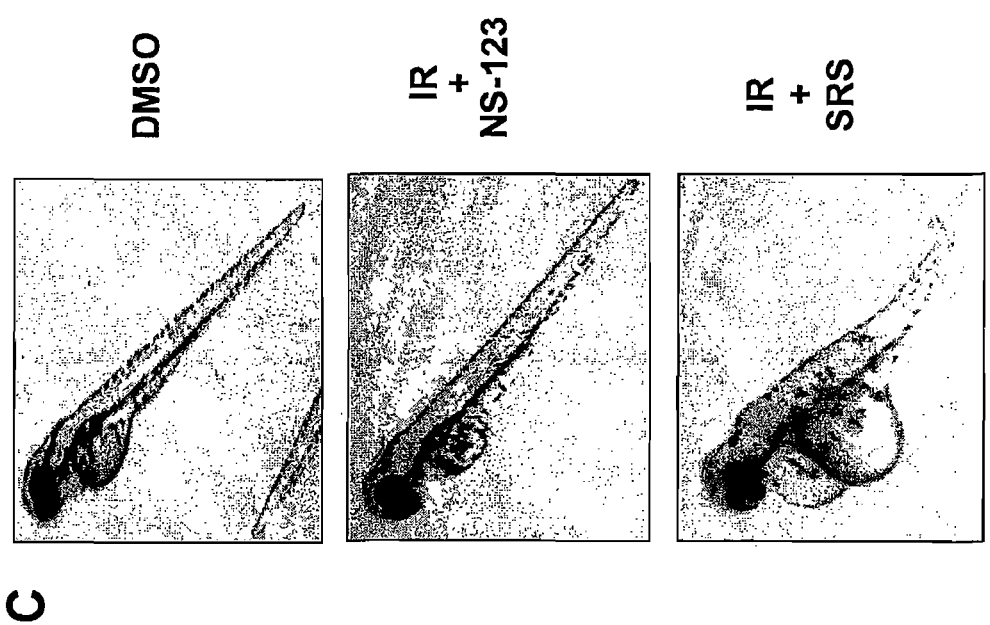

The objective of any combination of therapeutic agents is to achieve an improved therapeutic result, which is a function both of tumor response and of normal tissue damage. No improvement in the therapeutic result of IR is gained utilizing a drug that increases the sensitivity of both tumor and normal cells to the same extent. Thus, the radiosensitizing effect of NS-123 on normal tissues was investigated in two models. First, an MTS assay was performed utilizing NHA, which represents the normal cell counterpart of the U251 glioma cell lines. As shown in FIG. 5A, there was no significant increase in radiosensitization seen with either 8 hours or 12 hours pretreatment with 5 µM NS-123 compared to DMSO treated cells.

Example 5

Effects of NS-123 on Embryonic Development and Survival

The radiosensitizing effects of NS-123 on human cancer cells but not normal cells prompted us to examine the potential of NS-123 in vivo. Zebra fish (ZF) (*Danio rerio*) embryos provide an unique vertebrate model that is ideal for the screening of therapeutic agents because of their close genetic and physiological homology to upper level vertebrates such as mammals, their rapid embryonic development, optical clarity, and suitability for investigations regarding the effects of radiation and radiosensitizers (Geiger et al., 2006, Cancer Res. 66:8172-8181; McAleer et al., 2005, Int. J. Radiat. Oncol. Biol. Phys. 61:10-13). These features allow the efficient screening of novel drugs and observation of effects on specific organs without the need for euthanization and necroscopy. The ZF embryos were pretreated for 8 hours with 5 µM NS-123 prior to 6 Gy of radiation. As shown in FIGS. 5B and 5C, NS-123 did not appreciably impede normal embryonic development or viability. In contrast, staurosporine, a potent radiosensitizer with effects too general to be used clinically, greatly diminished the viability and development of the ZF embryos.

Example 6

NS-123 Radiosensitizes U251 Cells Transplanted into ZF Embryos

Figure 6:
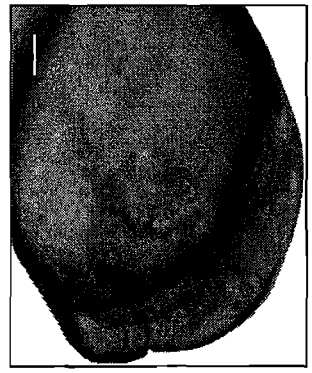
FIG. 6, comprising
Figure 6:
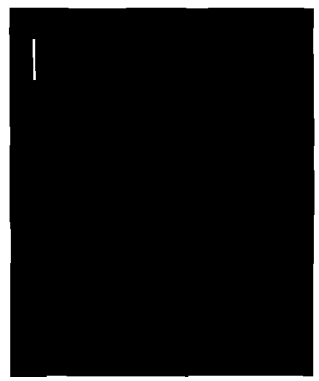
Figure 6:
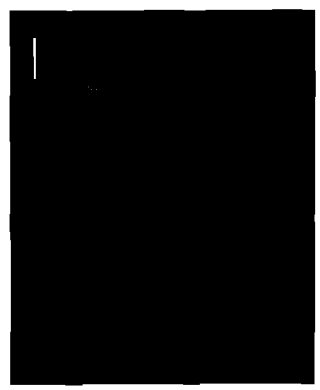
Figure 6:
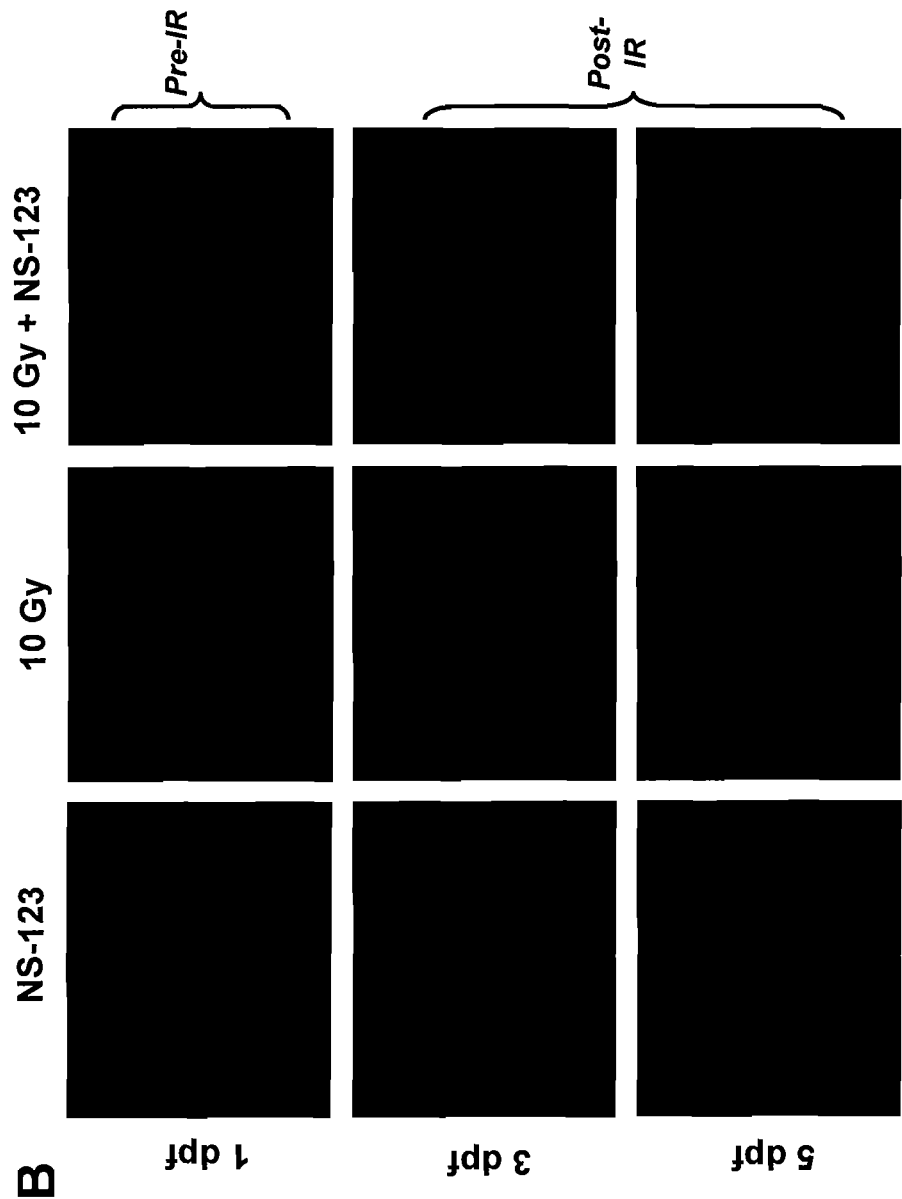
Figure 6:
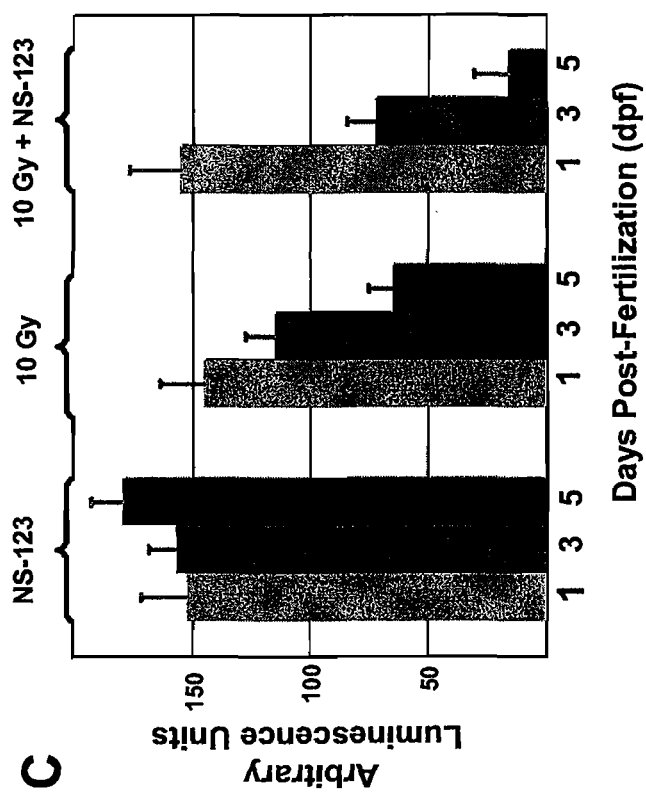

Human cancer cells can be transplanted into ZF embryos through microinjection (Lee et al., 2005, Dev. Dyn. 2233:1560-1570; Haldi et al., 2006, Angiogenesis 9:139-151; Mizgireuv et al., 2006, Cancer Res. 66:3120-3125). These human cancer cells will then proliferate, nourished by the nutrients circulating through the embryos. U251 cells expressing red fluorescent protein (RFP) were transplanted into ZF embryos; the RFP allowed the U251 cells to be distinguished from the background tissues of the embryos (FIG. 6A, left panel). The transparency and ex utero development of the ZF embryos facilitates the tracking and counting in real time of the transplanted human cells, again without the need for euthanization and necroscopy (FIG. 6A, middle and right panels). The U251 cells were transplanted into the embryonic yolk sac of 4.5 hpf embryos, treated with NS-123 and irradiated at 24 hpf. The embryos were subsequently examined for fluorescence on sequential days following irradiation. As shown in FIG. 6B, treatment of the embryos with NS-123 alone did not have any significant effect on the size of the U251 xenografts at 3 or 5 dpf. The U251 cells irradiated in the absence of NS-123 showed some regression at 3 and 5 dpf, whereas markedly fewer cells irradiated in the presence of NS-123 are survived at 5 dpf. Quantitation of these results using 10 embryos/condition/experiment and assessing the relative fluorescence demonstrated a faster decrease in luminescence compared to the irradiated-only control, indicating the more rapid extinction of fluorescence in the embryo irradiated in the presence of NS-123 (FIG. 6C). These data demonstrate the radiosensitizing potential of NS-123 in vivo.

Example 7

NS-123 is Well Tolerated in Nu/Nu (Nude) Mice

Figure 7:
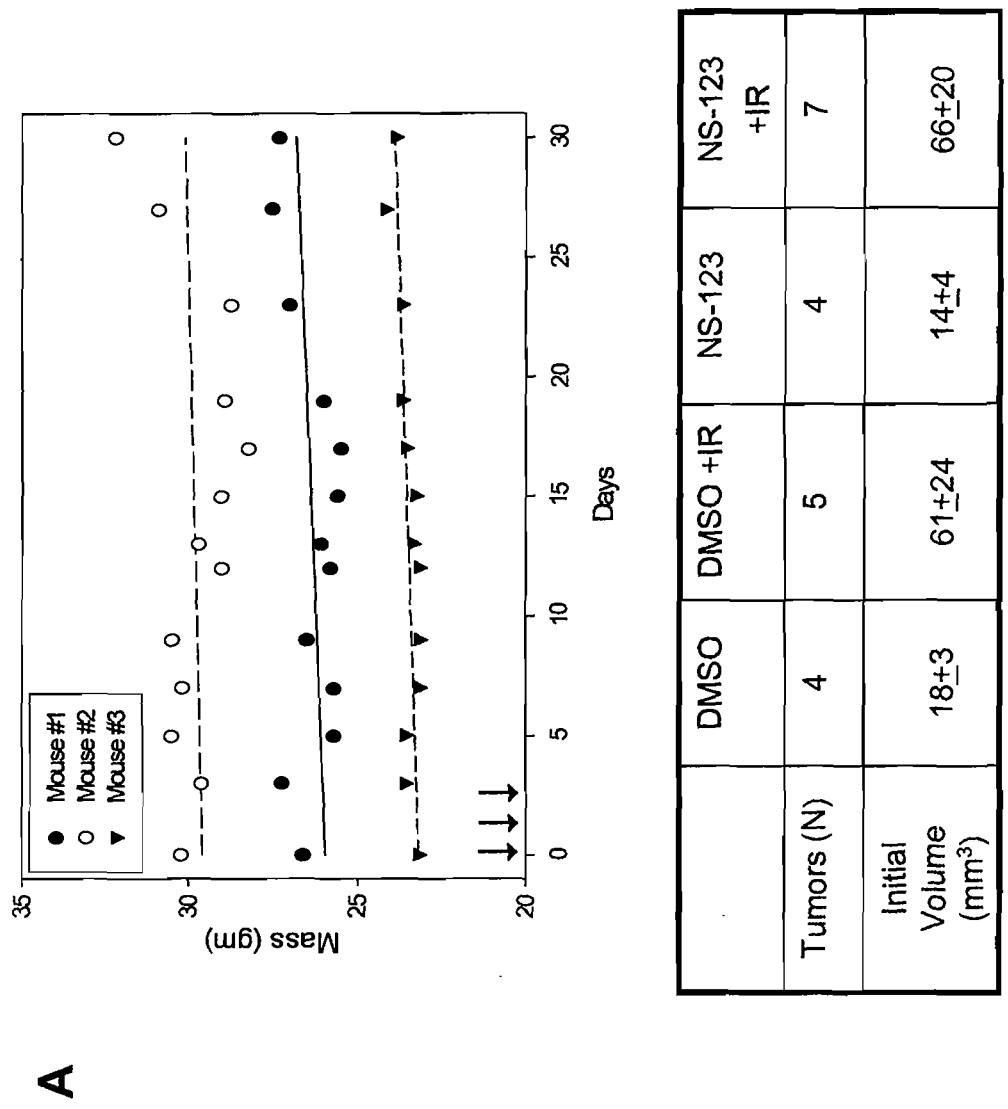
FIG. 7, comprising
Figure 7:
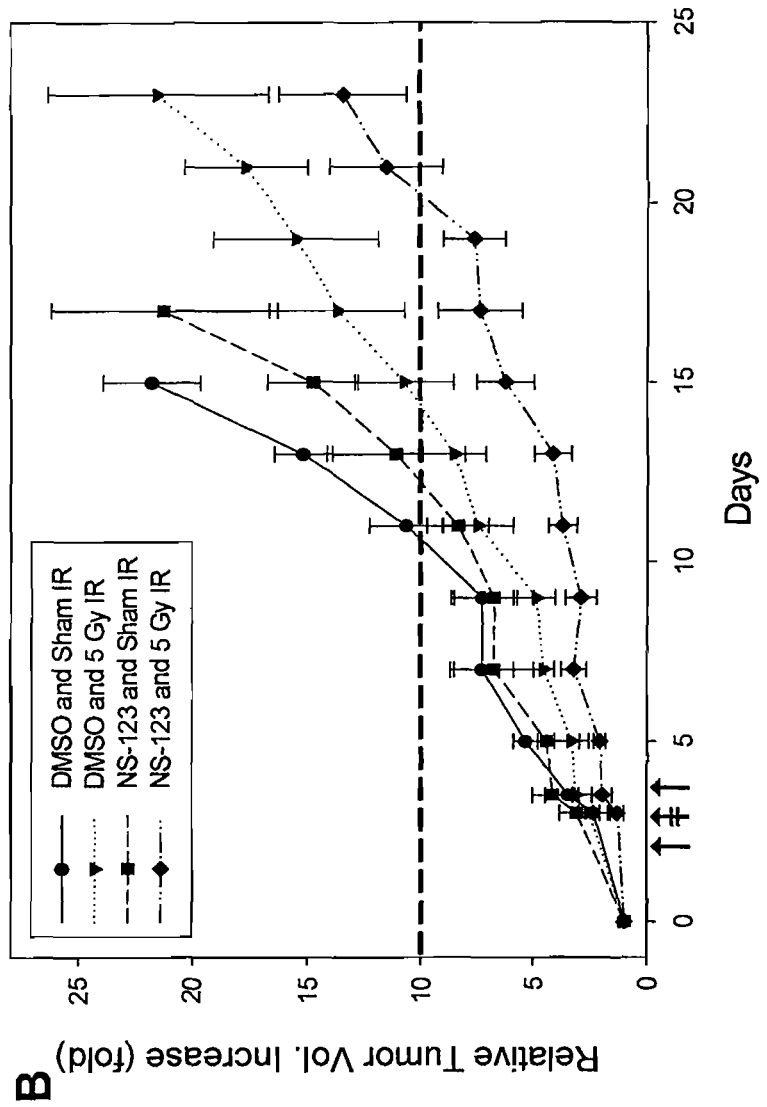

The ZF results suggest that NS-123 has low toxicity in higher order vertebrates. To test this hypothesis, 50 mg/kg (i.p.) was administered to nude mice for 3 consecutive days. Clinical signs of drug toxicity and lethality were not observed over the following 30 days. As seen in FIG. 7A, all mice gained weight. Furthermore, both gross and histopathological examination did not reveal any evidence suggestive of NS-123 associated toxicity. With these results, 50 mg/kg NS-123×3 days was considered to be an acceptable treatment regimen for further investigation to test the radiosensitization of NS-123 in mice.

Example 8

NS-123 Induces In Vivo Radiosensitization of U251 Tumors Implanted in Nu/Nu Nude Mice To investigate in a more sophisticated model the radiosensitization observed by NS-123 in ZF, a growth delay assay of U251 tumors xenografts in nu/nu nude mice was performed. Mice were treated for 3 consecutive days with either NS-123 or DMSO (i.p.) and received either 5 Gy IR or Sham IR 4 hours after the second injection (see Table at the bottom FIG. 7A). As seen in FIG. 7B, the mean time to reach Relative Tumor Volume (RTV)=10 was 10 days in the DMSO group, 12 days in the NS-123 group, 14 days in the DMSO+IR group, and 20 days in the NS-123+IR group which translates in an in vivo radiosensitizer enhancement ratio for NS-123 of 2.0. The results show that NS-123 can significantly increase the IR-induced tumor growth delay without significant toxicity in vivo. Furthermore, they provide additional support for the use of the novel ZF xenograft model as a faster, more economical screening tool for potential in vivo radiosensitizing activity of lead compounds.

Example 9

Figure 8:
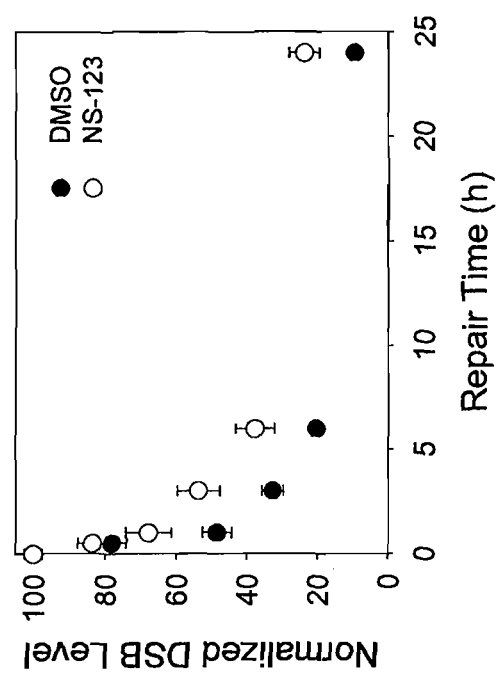
FIG. 8, comprising
Figure 8:
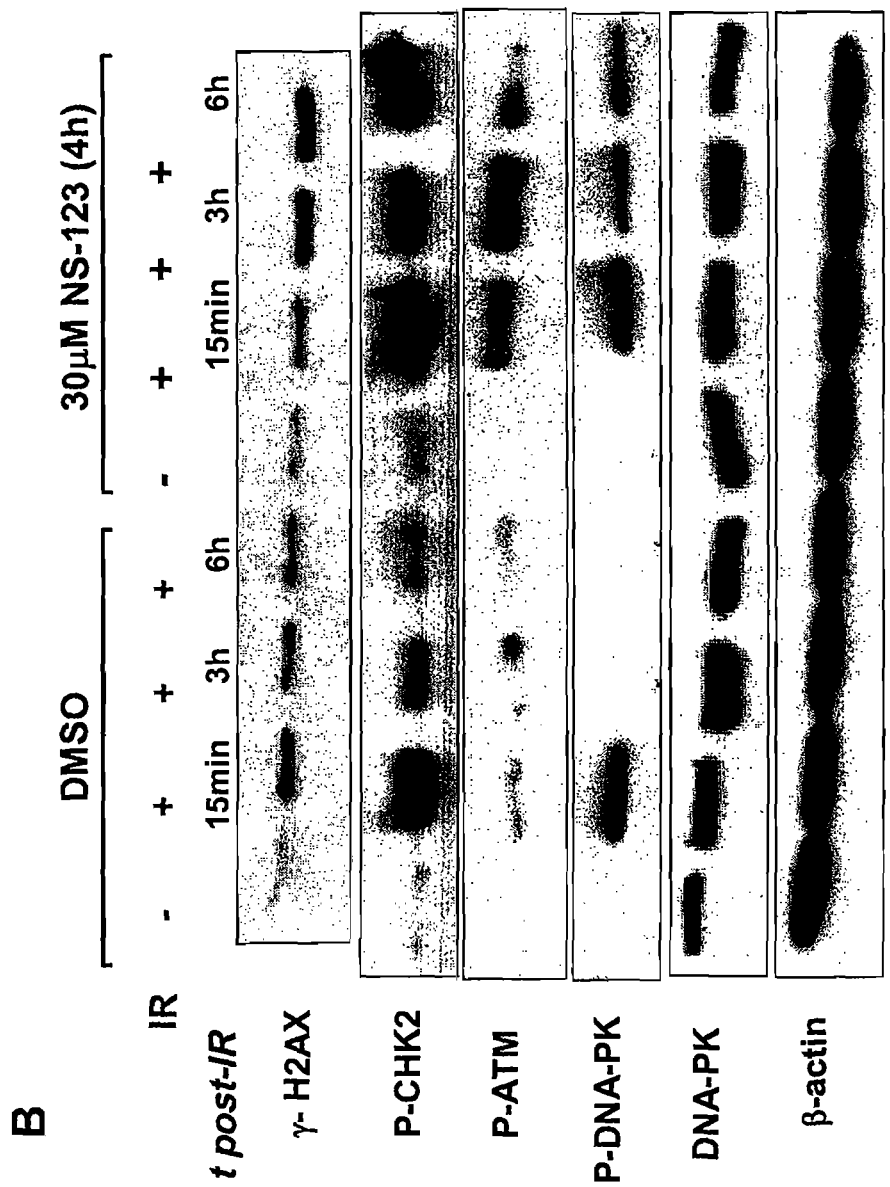

NS-123 Inhibits dsDNA Break Repair and Prolongs dsDNA Damage-Dependent Signaling Following Radiation As a first step in understanding the mechanism of the radiosensitizing activity of NS-123, the processing of DSBs in U251 cells treated with 30 µM NS-123 or DMSO (control) was measured using an adaptation of PFGE. When plated at high density (required to obtain amount of sufficient protein), a 4 hour, 30 µM dose of NS-123 induced comparable radiosensitization as a 5 µM, 12 hour preincubation dose on low-density plated cells (data not shown). Therefore, a 4 hour, 30 µM NS-123 treatment for experiments analyzing the effects of NS-123 on DSB repair and immunoblotting was used (see below) which require a significant quantity of cells. As shown in FIG. 8A, the initial number of dsDNA breaks was not affected by NS-123 (NS-123-treated: 88.5±5.3 DSBs/Gbp, DMSO-treated: 84.8±3.8 DSBs/Gbp). However, the processing of DSBs in NS-123 treated-U251 cells was significantly compromised. The NS-123-treated U251 cells showed not only slower repair kinetics but also incomplete repair of DSBs even after 24 hours. Specifically, the DMSO treated cells show almost complete repair of DSBs at 24 hours (~9% of their initial damage) while the NS-123 treated U251 cells show ~25% residual damage compared to their initial levels.

In response to DNA DSB, inactive ataxia telangiectasia (A-T) mutated protein undergoes autophosphorylation, including at serine 1981 (termed P-ATM) (Bakkenist et al., 2003, Nature 421:499-506; Kozlov et al., 2002, Proc. Natl. Acad. Sci. U.S.A. 99:8173-8178). The active ATM protein migrates to the sites of damage and phosphorylates the histone variant H2AX at serine 139 (termed γ-H2AX). The levels of γ-H2AX decrease following repair of the DNA damage (Bassing et al., 2002, Proc. Natl. Acad. Sci. U.S.A. 99:8173-8178; Rogakou et al., 1998, J. Biol. Chem. 273:5858-5868; Siino et al., 2002, FEBS Lett. 527:105-108), and therefore γ-H2AX can serve as a surrogate quantitative measure of DSBs (Olive et al., 2004, Int. J. radiat. Oncol. Biol. Phys. 58:331-335; Nazarov et al., 2003, Radiat. Res. 160:309-317; Macphail et al., 2003, Int. J. Radiat. Biol. 79:351-358; Bonner et al., 2003, Proc. Natl. Acad. Sci. U.S.A. 100:4973-4975). CHK2 is a protein kinase that targets two critical effectors operating in distinct branches of the $G_1$ checkpoint, the Cdc25A phosphatase and the p53 transcription factor, both of which prevent entry of cells into S phase with damaged DNA (Lukas et al., 2004, DNA Repair (Amst.) 3:997-1007). P-ATM phosphorylates CHK2 at threonine 68 (termed P-CHK2). Both P-CHK2 and γ-H2AX increase immediately after IR and gradually decreases as DSBs become repaired (Matsuoka et al., 1998, Science 282:1893-1990; Pandita et al., 2000, Oncogene 19:1386-1391). Similar to ATM, the DNA-dependent protein kinase catalytic subunit (termed P-DNA-PKcs) can be phosphylated by DNA DSB resulting from IR and will also phosphorylate both γ-H2AX and P-CHK2 (Li et al., 2005, J. Biol. Chem. 280:12041-12050; Stiff et al., 2004, Cancer Res. 64:2390-2396).

The levels of γ-H2AX, P-CHK2, P-ATM, and P-DNA-PKcs were assayed in U251 cells by immunoblotting at various time points after IR. Cells were treated with DMSO (control) or 30 μM NS-123 for 4 hours prior to IR. FIG. 8B shows representative results. In the absence of NS-123, IR caused a significant increase in both γ-H2AX, P-CHK2, P-DNA-PKcs, and P-ATM at 15 minutes, which decreased and returned to baseline by 6 hours. In contrast, in cells treated with NS-123, at 6 hours after IR, (a time at which more than 90% of DSBs should have been repaired), U251 cells exhibited substantially higher levels of both γ-H2AX X, P-CHK2, P-DNA-PKcs, and P-ATM suggesting that unrepaired DSBs accumulate in the presence NS-123. Even though the precise target of NS-123 is currently not known, these results strongly point towards an inhibition of DNA damage signaling pathway as a potential mechanism for radiosensitization.

Example 10

Effect of NS-160 in a MIT Assay

Figure 9:
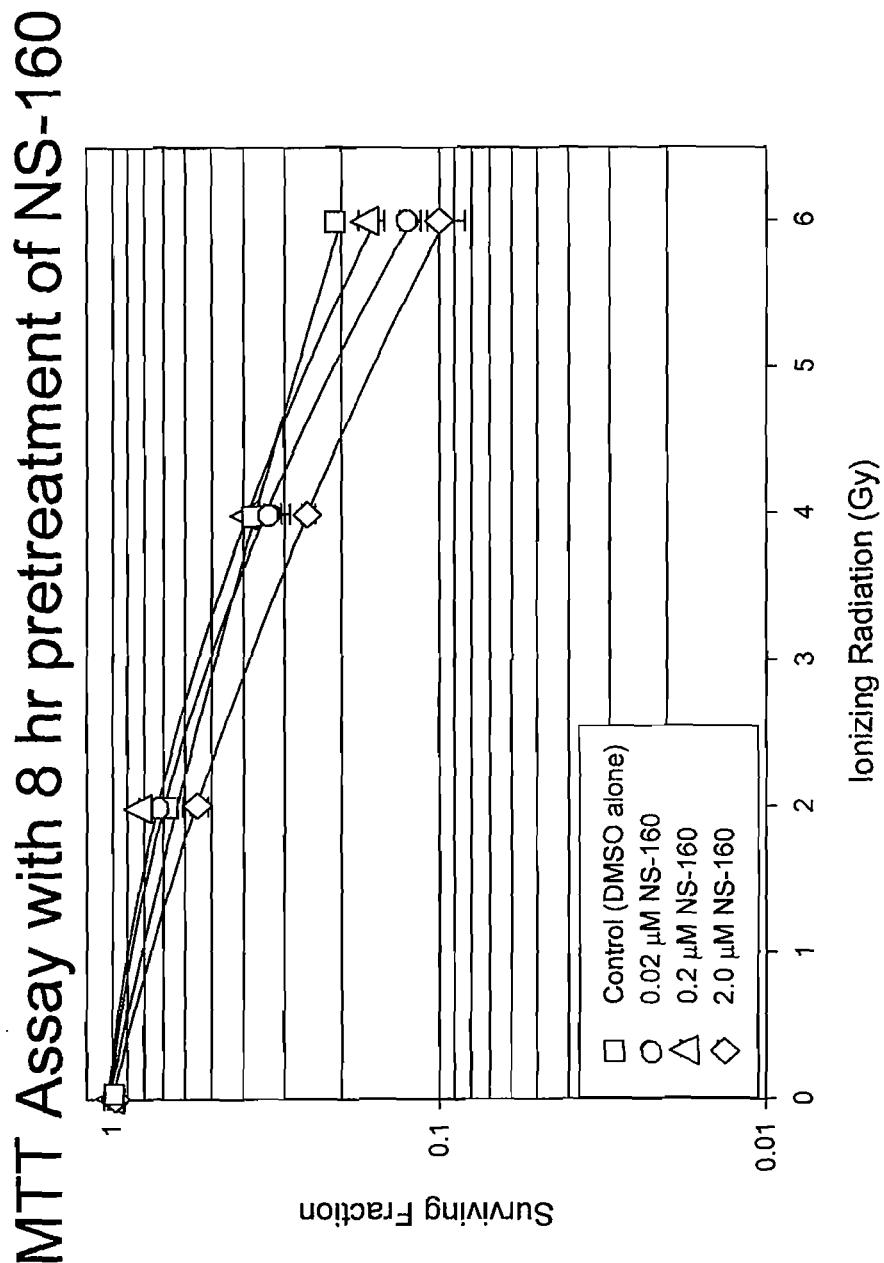
FIG. 9 is a graph depicting the data obtained from a MIT clonogenic assay demonstrating the radiosensitizing effects of NS-160. Cells were pre-treated with control, 0.02 μM, 0.2 μM, or 2.0 μM of NS-160 in vitro prior to exposure to various dosages of ionizing radiation. Results represent the average±S.E.M.

The dose-dependent radiosensitizing effects of NS-160 were investigated using an 8 hour pretreatment of 0.02 μM, 0.2 μM, and 2.0 μM NS-160 in U251 cells (FIG. 9). Radiosensitization was evident at 0.2 μM at the IR dose of 4 Gy used in fractionated radiation schemes. Therefore, NS-160 can act as a true radiosensitizer at low μM concentrations.

Example 11

Comparison of Compound 1D and Compound 2C

Figure 10:
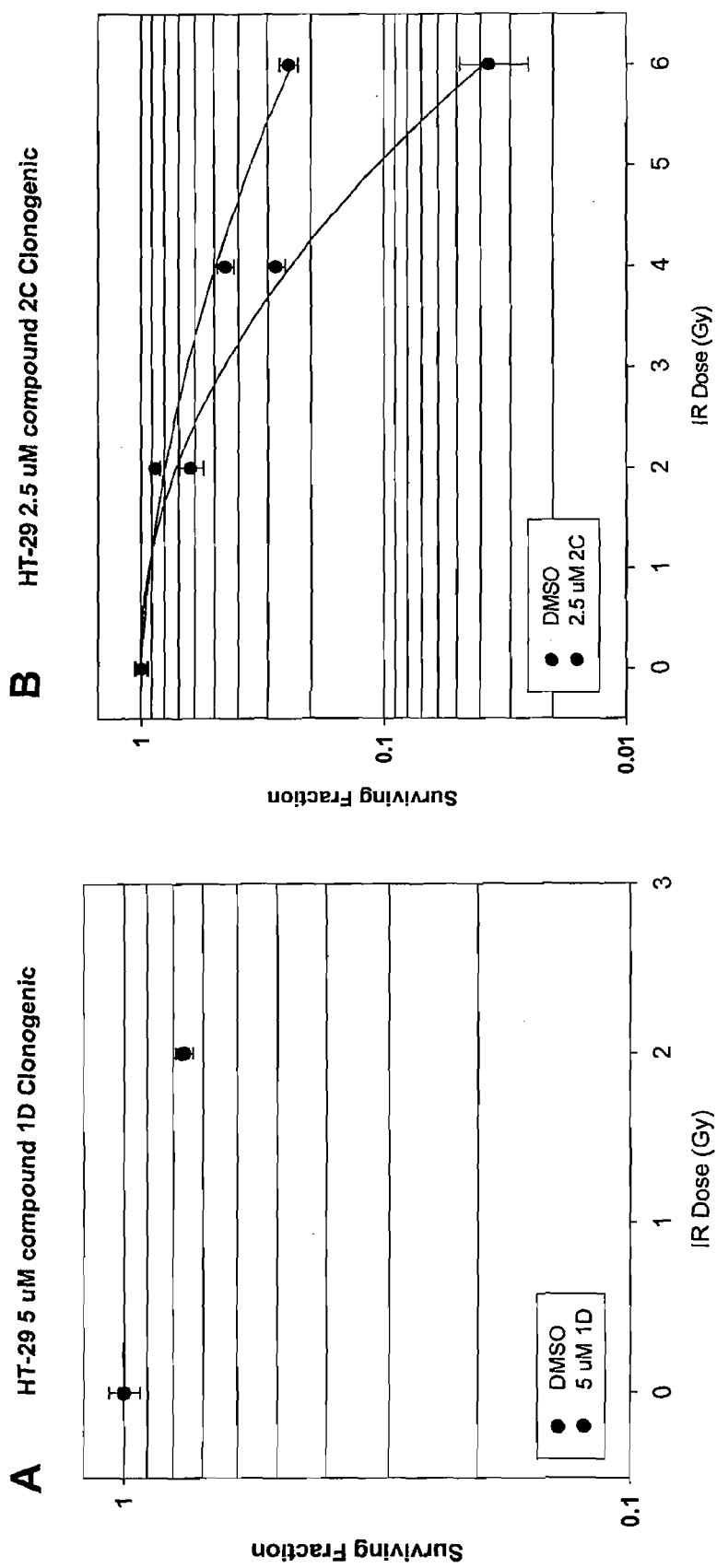
FIG. 10, comprising

Clonogenic survival of HT-29 human colorectal tumor cells in the presence of two chemical analogs of NS-123. FIG. 10A is a graph depicting a comparison of clonogenic survival in the presence of Compound 1D (5 microM) or the vehicle control DMSO. FIG. 10B is a graph depicting a comparison of clonogenic survival in the presence of Compound 2C (2.5 microM) or the vehicle control DMSO. In both cases, cells were pretreated with the compounds or DMSO vehicle control for 4 hours prior to treatment with ionizing radiation at the indicated doses. Compound 2C is at least 2-fold more potent than NS-123, while compound 1-D (which lacks bromine in the 4' position) is inert as a radiosensitizer.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a mammal diagnosed with cancer, said method comprising administering to said mammal a therapeutically effective amount of a pharmacological composition comprising a compound of formula (I):

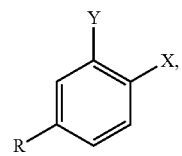

wherein:
Y is $NO_2$, $NR^1_3$, CN, CHO, $C(O)R^1$ or $CF_3$;
X is H, F, Cl, Br or I;
R is CN, CHO, $C(O)R^1$, $C(O)NH_2$, $C(O)NHR^1$, $C(O)NR^1R^2$, $S(O)_mR^1$, $S(O)_2NH_2$, $S(O)_2NHR^1$, $S(O)_2NR^1R^2$, $P(O)(OH)R^1$, $C(O)OH$, or $C(O)OR^1$;
$R^1$ and $R^2$ each independently is $CH_3$, $CH_2CH_3$, $CH_2CH_2CH_3$, $CH_2CH_2CH_2CH_3$, $CH(CH_3)_2$, or $C(CH_3)_3$; and
m is an integer of 0, 1 or 2;
or a pharmaceutically acceptable salt,
wherein said composition contacts a cancer cell or tumor in said mammal, thereby making said cancer cell or tumor more susceptible to the effects of ionizing radiation,
wherein said cancer is at least one selected from the group consisting of glioma, colorectal cancer and non-small cell lung cancer.

2. The method of claim 1, wherein said composition is administered before, during, or after said mammal receives radiation therapy, or a combination thereafter.

3. The method of claim 1, wherein said mammal is a human.

4. A method of treating a mammal diagnosed with cancer, said method comprising administering to said mammal a therapeutically effective amount of a composition comprising Formula I,

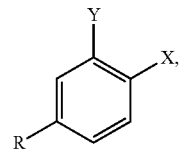

wherein Y=$NO_2$, R=$C(O)R^1$, $R^1$=$CH_2CH_3$, and X=I, or a pharmaceutically acceptable salt thereof, wherein said composition contacts a cancer cell or tumor in said mammal, thereby making said cancer cell or tumor more susceptible to the effects of ionizing radiation,
wherein said cancer is at least one selected from the group consisting of glioma, colorectal cancer and non-small cell lung cancer.

5. The method of claim 4, wherein said composition is administered before, during, or after said mammal receives radiation therapy, or a combination thereafter.

6. The method of claim 4, wherein said mammal is a human.

7. A method of treating a mammal diagnosed with cancer, said method comprising administering to said mammal a therapeutically effective amount of a composition comprising Formula I,

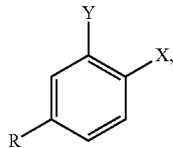

(I)

wherein Y=$NO_2$, R=$S(O)_2R^1$, $R^1$=$CH_2CH_3$, and X=F or I, or a pharmaceutically acceptable salt thereof,
wherein said composition contacts a cancer cell or tumor in said mammal, thereby making said cancer cell or tumor more susceptible to the effects of ionizing radiation
wherein said cancer is at least one selected from the group consisting of glioma, colorectal cancer and non-small cell lung cancer.

8. The method of claim 7, wherein said composition is administered before, during, or after said mammal receives radiation therapy, or a combination thereafter.

9. The method of claim 7, wherein said mammal is a human.

10. A method of treating a mammal diagnosed with cancer, said method comprising administering to said mammal a therapeutically effective amount of a composition comprising Formula I,

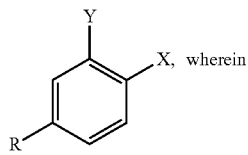

(I)

Y=$NO_2$, R=$P(O)(OH)R^1$, $R^1$=$CH_2CH_3$, and X=F, Cl, Br, H, or I, or a pharmaceutically acceptable salt thereof,
wherein said composition contacts a cancer cell or tumor in said mammal, thereby making said cancer cell or tumor more susceptible to the effects of ionizing radiation,
wherein said cancer is at least one selected from the group consisting of glioma, colorectal cancer and non-small cell lung cancer.

11. The method of claim 10, wherein said composition is administered before, during, or after said mammal receives radiation therapy, or a combination thereafter.

12. The method of claim 10, wherein said mammal is a human.

* * * * *